US012612393B2

(12) United States Patent
Utaka

(10) Patent No.: US 12,612,393 B2
(45) **Date of Patent: *Apr. 28, 2026**

(54) BENZOXAZINE COMPOUND, RESIN RAW MATERIAL COMPOSITION CONTAINING THE SAME, CURABLE RESIN COMPOSITION, AND CURED PRODUCT THEREOF

(71) Applicant: HONSHU CHEMICAL INDUSTRY CO., LTD., Chuo-ku (JP)

(72) Inventor: Yoshimi Utaka, Wakayama (JP)

(73) Assignee: HONSHU CHEMICAL INDUSTRY CO., LTD., Tokyo (JP)

(*) Notice: Subject to any disclaimer, the term of this patent is extended or adjusted under 35 U.S.C. 154(b) by 401 days.

This patent is subject to a terminal disclaimer.

(21) Appl. No.: 18/262,295

(22) PCT Filed: Jan. 24, 2022

(86) PCT No.: PCT/JP2022/002314

§ 371 (c)(1),
(2) Date: Jul. 20, 2023

(87) PCT Pub. No.: WO2022/163553

PCT Pub. Date: Aug. 4, 2022

(65) Prior Publication Data

US 2024/0101543 A1 Mar. 28, 2024

(30) Foreign Application Priority Data

Jan. 29, 2021 (JP) ................................ 2021-013397

(51) Int. Cl.
*C07D 413/10* (2006.01)
*C08J 7/12* (2006.01)
*C08K 5/357* (2006.01)

(52) U.S. Cl.
CPC .............. *C07D 413/10* (2013.01); *C08J 7/12* (2013.01); *C08K 5/357* (2013.01)

(58) Field of Classification Search
CPC ........ C07D 413/10; C07D 265/16; C08J 7/12; C08K 5/357; C08L 101/00
See application file for complete search history.

(56) References Cited

U.S. PATENT DOCUMENTS

| | | |
|---|---|---|
| 9,120,763 B2 | 9/2015 | Wang et al. |
| 2007/0129509 A1 | 6/2007 | Li et al. |
| 2011/0189458 A1 | 8/2011 | Sudo et al. |
| 2018/0030264 A1 | 2/2018 | Wang et al. |

FOREIGN PATENT DOCUMENTS

| | | |
|---|---|---|
| CN | 107573496 A | 4/2020 |
| JP | 2011207805 A | 10/2011 |
| JP | 2011530570 A | 12/2011 |

(Continued)

OTHER PUBLICATIONS

CAS Registry No. 1980031-35-3 (which entered the STN database on Aug. 25, 2016). (Year: 2016).*
Musa; Polym. Bull. 2020, 77, 5439-5449. https://doi.org/10.1007/s00289-019-03026-0 (Year: 2020) (11 pages).
Requirement for Restriction/Election issued by U.S. Patent and Trademark Office, dated Dec. 12, 2025, for a co-pending U.S. Appl. No. 18/272,055. (11 pages).
A First Office Action with Search Report issued by the Patent Office of the People's Republic of China on Aug. 28, 2025, for Chinese counterpart application No. 202280011056.X (8 pages).
International Search Report (ISR) mailed Mar. 29, 2022, issued for International application No. PCT/JP2022/002314. (2 pages).

(Continued)

*Primary Examiner* — Kamal A Saeed
*Assistant Examiner* — Meghan C Heasley
(74) *Attorney, Agent, or Firm* — Law Office of Katsuhiro Arai

(57) ABSTRACT

A benzoxazine compound is represented by general formula (1):

(1)

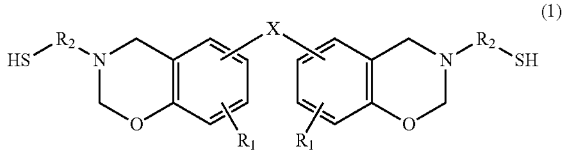

wherein $R_1$ represents a hydrogen atom or an alkyl group having 1 to 6 carbon atoms, $R_2$ represents a divalent group having 1 to 10 carbon atoms, and X represents a single bond, an oxygen atom, a sulfur atom, a sulfonyl group, a carbonyl group, or a divalent group represented by general formula (1a) or general formula (1b), and (1a)

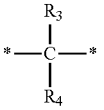

(1b)

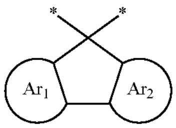

wherein $R_3$ and $R_4$ each independently represent hydrogen, an alkyl group having 1 to 10 carbon atoms, an alkyl halide group having 1 to 10 carbon atoms, or an aryl group having 6 to 12 carbon atoms, $R_3$ and $R_4$ are optionally bonded to each other to together form a cycloalkylidene group having 5 to 20 carbon atoms, $Ar_1$ and $Ar_2$ each independently represent an aryl group having 6 to 12 carbon atoms, and * represents a bonding position.

11 Claims, No Drawings

(56) References Cited

FOREIGN PATENT DOCUMENTS

| | | | |
|---|---|---|---|
| JP | 2014521720 | A | 8/2014 |
| KR | 1020150027861 | A | 3/2015 |
| WO | 2010018198 | A1 | 2/2010 |
| WO | 2019178547 | A1 | 9/2019 |

OTHER PUBLICATIONS

International Preliminary Report on Patentability, dated Feb. 27, 2024, for related international application PCT/JP2022/030421 (1 page).
Notification Concerning Transmittal of International Preliminary Report on Patentability, mailed Mar. 7, 2024, for related international application PCT/JP2022/030421 (1 page).
Notification of Transmittal of Translation of the International Preliminary Report on Patentability, mailed Mar. 7, 2024, for related international application PCT/JP2022/030421 (1 page).
Written Opinion of the International Searching Authority, mailed Sep. 27, 2022, for related international application PCT/JP2022/030421 (4 pages).
Ching et al., Synthesis of a Benzoxazine with Precisely Two Phenolic OH Linkages and the Properties of Its High-Performance Copolymers, Journal of Polymer Science, Part A: Polymer Chemistry, 2013, 51(12), pp. 2686-2694, DOI: 10.1002/pola.26661. (9 pages).
Devaraju et al., Polybenzoxazine-silica (PBZ-SiO2) hybrid nanocomposites through in situ sol-gel method, Journal of Sol-Gel Science and Technology, 2011, 60(1), pp. 33-40, DOI: 10.1007/s10971-011-2547-z. (8 pages).
Gilbert et al., Synthesis and characterization of new thermosetting polybenzoxazines with other functional groups in the network, Journal of Polymer Research. 2018, 25(5):114, pp. 1-12, DOI:10.1007/s10965-018-1501-y. (12 pages).
International Preliminary Report on Patentability, dated Jul. 31, 2023, for related international application PCT/JP2021/002324 (1 page).
International Preliminary Report on Patentability, dated Jul. 31, 2023, for related international application PCT/JP2022/002310 (1 page).
International Preliminary Report on Patentability, dated Jul. 31, 2023, for related international application PCT/JP2022/002311 (1 page).
International Search Report (ISR) mailed Mar. 29, 2022, issued for related International application No. PCT/JP2022/002310. (3 pages).
International Search Report (ISR) mailed Mar. 29, 2022, issued for related International application No. PCT/JP2022/002311. (2 pages).
International Search Report (ISR) mailed Mar. 29, 2022, issued for related International application No. PCT/JP2022/002324. (2 pages).
Notification Concerning Transmittal of International Preliminary Report on Patentability, mailed Aug. 10, 2023, for related international application PCT/JP2022/002324 (1 page).
Notification Concerning Transmittal of International Preliminary Report on Patentability, mailed Aug. 10, 2023, for related international application PCT/JP2022/002311 (1 page).
Notification Concerning Transmittal of International Preliminary Report on Patentability, mailed Aug. 10, 2023, for related international application PCT/JP2022/002310 (1 page).
Notification of Transmittal of Translation of the International Preliminary Report on Patentability, mailed Aug. 10, 2023, for related international application PCT/JP2022/002310 (1 page).
Notification of Transmittal of Translation of the International Preliminary Report on Patentability, mailed Aug. 10, 2023, for related international application PCT/JP2022/002311 (1 page).
Notification of Transmittal of Translation of the International Preliminary Report on Patentability, mailed Aug. 10, 2023, for related international application PCT/JP2022/00234 (1 page).
Vengatesan et al., Studies on Thermal and Dielectric Properties of Organo Clay and Octakis (dimethylsiloxypropylglycidylether) Silsesquioxane Filled Polybenzoxazine Hybrid Nanocomposites, Polymer Composites, 2011, 32(11), pp. 1701-1711, DOI: 10.1002/pc.21177. (11 pages).
Written Opinion of the International Searching Authority, mailed Mar. 29, 2022, for related international application PCT/JP2022/002324 (4 pages).
Written Opinion of the International Searching Authority, mailed Mar. 29, 2022, for related international application PCT/JP2022/002310 (3 pages).
Written Opinion of the International Searching Authority, mailed May 29, 2022, for related international application PCT/JP2022/002311 (3 pages).
International Preliminary Report on Patentability, dated Jul. 31, 2023, for corresponding international application PCT/JP2022/002314 (1 page).
Notification Concerning Transmittal of International Preliminary Report on Patentability, mailed Aug. 10, 2023, for corresponding international application PCT/JP2022/002314 (1 page).
Notification of Transmittal of Translation of the International Preliminary Report on Patentability, mailed Aug. 10, 2023, for corresponding international application PCT/JP2022/002314 (1 page).
Written Opinion of the International Searching Authority, mailed Mar. 29, 2022, for corresponding international application PCT/JP2022/002314 (3 pages).
Musa et al., The effect of curing temperatures on the thermal behaviour of new polybenzoxazine-modified epoxy resin, Polymer Bulletin, 2020, 77, 5439-5449 (pub'd Nov. 22, 2019) (Year: 2020) (11 pages).
Non-Final Office Action issued by U.S. Patent and Trademark Office, dated Feb. 24, 2026, for a co-pending U.S. Appl. No. 18/272,055. (40 pages).

* cited by examiner

BENZOXAZINE COMPOUND, RESIN RAW MATERIAL COMPOSITION CONTAINING THE SAME, CURABLE RESIN COMPOSITION, AND CURED PRODUCT THEREOF

CROSS-REFERENCE TO RELATED APPLICATIONS

This application is the U.S. National Phase under 35 U.S.C. § 371 of International Application PCT/JP2022/002314, filed Jan. 24, 2022, which claims priority to Japanese Patent Application No. JP2021-013397, filed Jan. 29, 2021. The International Application was published under PCT Article 21(2) in a language other than English.

TECHNICAL FIELD

The present invention relates to a novel benzoxazine compound, a resin raw material composition containing the benzoxazine compound, a curable resin composition, and a cured product thereof. The invention particularly relates to a novel benzoxazine compound having benzoxazine rings at both ends of a linking group and further having a thiol group, a resin raw material composition containing the benzoxazine compound, a curable resin composition, and a cured product thereof.

BACKGROUND ART

Benzoxazine compounds are known as thermosetting resin raw materials that, when heated, undergo ring-opening polymerization of a benzoxazine ring to cure without producing any volatile by-products, and are used as raw materials of a molded body usable as a material for an insulating substrate, a liquid crystal alignment agent, a resin composition for semiconductor sealing, and the like.

On the other hand, benzoxazine compounds typically have relatively high curing temperatures, and to achieve lower polymerization temperatures, catalysts, polymerization accelerators, and highly reactive benzoxazine compounds have recently been developed. Among the highly reactive benzoxazine compounds, a hydroxyl-functionalized benzoxazine composition having a structure in which a hydroxyl group is introduced has been reported (PTL 1).

CITATION LIST

Patent Literature

PTL 1: Japanese Unexamined Patent Application Publication (Translation of PCT Application) No. 2011-530570

SUMMARY OF INVENTION

Technical Problem

To lower the temperature during the process of molding a thermosetting resin, thereby achieving higher efficiency due to reduced time of heating and cooling and saved energy and suppressing material thermal degradation due to exposure to high temperature during polymerization, excellent materials that can cure under low temperature conditions are demanded.

In addition, to lower the temperatures during mixing with other thermosetting resin monomers or various additives and during the process of molding a thermosetting resin, materials having low melt temperatures are required.

It is an object of the present invention to provide a novel benzoxazine compound that can cure under low temperature conditions, a resin raw material composition containing the benzoxazine compound, a curable resin composition, and a cured product thereof.

Solution to Problem

To achieve the above object, the present inventors have conducted intensive studies and found that a novel benzoxazine compound obtained by using a bisphenol compound as a raw material, having benzoxazine rings at both ends of a linking group, and further having a thiol group can cure under low temperature conditions, thereby completing the present invention.

The present invention is as follows.

1. A benzoxazine compound represented by general formula (1).

[Chem. 1]

(1)

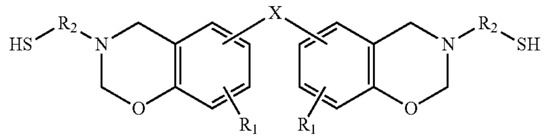

(In the formula, $R_1$ represents a hydrogen atom or an alkyl group having 1 to 6 carbon atoms, $R_2$ represents a divalent group having 1 to 10 carbon atoms, and X represents a single bond, an oxygen atom, a sulfur atom, a sulfonyl group, a carbonyl group, or a divalent group represented by general formula (1a) or general formula (1b).)

[Chem. 2]

(1a)

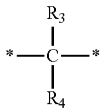

(1b)

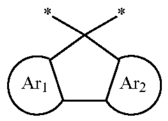

(In general formulae (1a) and (1b), $R_3$ and $R_4$ each independently represent hydrogen, an alkyl group having 1 to 10 carbon atoms, an alkyl halide group having 1 to 10 carbon atoms, or an aryl group having 6 to 12 carbon atoms, $R_3$ and $R_4$ are optionally bonded to each other to together form a cycloalkylidene group having 5 to 20 carbon atoms, $Ar_1$ and $Ar_2$ each independently represent an aryl group having 6 to 12 carbon atoms, and * represents a bonding position.)

2. A resin raw material composition containing the benzoxazine compound according to 1.
3. A curable resin composition containing the benzoxazine compound according to 1. or the resin raw material composition according to 2.

4. The curable resin composition according to 3., containing the benzoxazine compound according to 1. or the resin raw material composition according to 2., and at least one selected from the group consisting of epoxy resins, benzoxazine compounds other than the benzoxazine compound represented by general formula (1), phenol resins, and bismaleimide compounds.
5. A cured product obtained by curing the curable resin composition according to 3. or 4.

Advantageous Effects of Invention

The novel benzoxazine compound according to the present invention, as compared to benzoxazine compounds having a hydroxy group known in the art, can cure at a low temperature and can melt at a low temperature.

Thus, the use of the novel benzoxazine compound according to the present invention can lower the temperatures during mixing with other thermosetting resin monomers or various additives and during the process of molding a thermosetting resin, enabling higher efficiency due to reduced time of heating and cooling and saved energy, and can suppress material thermal degradation due to exposure to high temperature during mixing with other thermosetting resin monomers and various additives and during polymerization, which is very useful.

The novel benzoxazine compound, the resin raw material composition containing the benzoxazine compound, the curable resin composition, and the cured product thereof in the present invention are suitable for use as resin raw materials for varnishes that can be applied to various substrates, prepregs impregnated with varnishes, print circuit boards, sealants for electronic components, electrical and electronic molded parts, automotive parts, laminated materials, paints, resist inks, and the like.

DESCRIPTION OF EMBODIMENTS

<Novel Benzoxazine Compound According to Present Invention>

A novel benzoxazine compound according to the present invention is represented by general formula (1).

[Chem. 3]

(1)

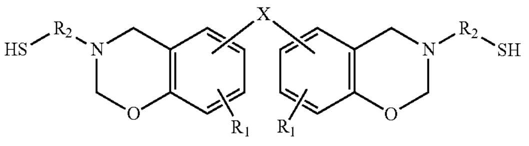

(In the formula, $R_1$ represents a hydrogen atom or an alkyl group having 1 to 6 carbon atoms, $R_2$ represents a divalent group having 1 to 10 carbon atoms, and X represents a single bond, an oxygen atom, a sulfur atom, a sulfonyl group, a carbonyl group, or a divalent group represented by general formula (1a) or general formula (1b).)

[Chem. 4]

(1a)

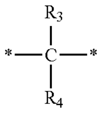

-continued (1b)

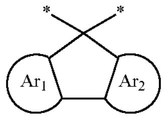

(In general formulae (1a) and (1b), $R_3$ and $R_4$ each independently represent hydrogen, an alkyl group having 1 to 10 carbon atoms, an alkyl halide group having 1 to 10 carbon atoms, or an aryl group having 6 to 12 carbon atoms, $R_3$ and $R_4$ are optionally bonded to each other to together form a cycloalkylidene group having 5 to 20 carbon atoms, $Ar_1$ and $Ar_2$ each independently represent an aryl group having 6 to 12 carbon atoms, and * represents a bonding position.)

$R_1$ in general formula (1) is preferably a hydrogen atom or an alkyl group having 1 to 4 carbon atoms, more preferably a hydrogen atom or an alkyl group having 1 carbon atom (methyl group), particularly preferably a hydrogen atom. When R 1 is not a hydrogen atom, the bonding position thereof is preferably the ortho position on the benzene ring relative to the oxygen atom of each benzoxazine ring.

$R_2$ in general formula (1) is a divalent group having 1 to 10 carbon atoms, and specific examples include linear or branched alkylene groups having 1 to 10 carbon atoms or alkylene groups including a cyclic alkane, such as a methylene group, an ethylene group, a propane-1,2-diyl group, a propane-1,3-diyl group, a butane-1,4-diyl group, a pentane-1,5-diyl group, a hexane-1,6-diyl group, a cyclohexane-1,3-diyl group, and a cyclohexane-1,4-diyl group; alkylidene groups having 1 to 10 carbon atoms such as an ethylidene group, a propylidene group, an isopropylidene group, a butylidene group, a cyclopentylidene group, and a cyclohexylidene group; a phenylene group; and divalent groups containing a benzene ring and having 1 to 10 carbon atoms, such as groups represented by the following formulae.

[Chem. 5]

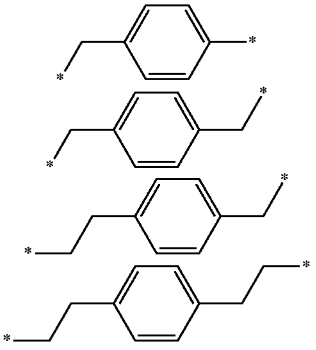

(In the formulae, * represents a bonding position.)

Of these, $R_2$ is preferably a linear or branched alkylene group having 1 to 10 carbon atoms, an alkylene group including a cyclic alkane, or an alkylidene group having 1 to 10 carbon atoms, more preferably a linear or branched alkylene group having 1 to 10 carbon atoms or an alkylene group including a cyclic alkane, still more preferably a linear or branched alkylene group having 1 to 6 carbon atoms or an alkylene group including a cyclic alkane, particularly preferably a linear or branched alkylene group having 1 to 4 carbon atoms.

When X in general formula (1) is represented by general formula (1a), $R_3$ and $R_4$, independently of each other, are more preferably hydrogen, an alkyl group having 1 to 6 carbon atoms, an alkyl halide group having 1 to 6 carbon atoms, or an aryl group having 6 to 12 carbon atoms, still more preferably hydrogen, an alkyl group having 1 to 4 carbon atoms, a trifluoromethyl group, or an aryl group having 6 to 8 carbon atoms, particularly preferably hydrogen, an alkyl group having 1 to 4 carbon atoms, or a phenyl group.

$R_3$ and $R_4$ may be bonded to each other to together form a cycloalkylidene group having 5 to 20 carbon atoms, and in this case, a cured product obtained using this benzoxazine compound has high heat resistance. The cycloalkylidene group having 5 to 20 carbon atoms may include a branched-chain alkyl group. The cycloalkylidene group preferably has 5 to 15 carbon atoms, more preferably has 6 to 12 carbon atoms, and particularly preferably has 6 to 9 carbon atoms.

Specific examples of the cycloalkylidene group include a cyclopentylidene group (5 carbon atoms), a cyclohexylidene group (6 carbon atoms), a 3-methylcyclohexylidene group (7 carbon atoms), a 4-methylcyclohexylidene group (7 carbon atoms), a 3,3,5-trimethylcyclohexylidene group (9 carbon atoms), a cycloheptylidene group (7 carbon atoms), a bicyclo[2.2.1]heptane-2,2-diyl group (7 carbon atoms), a 1,7,7-trimethylbicyclo[2.2.1]heptane-2,2-diyl group (10 carbon atoms), a 4,7,7-trimethylbicyclo[2.2.1]heptane-2,2-diyl group (10 carbon atoms), a tricyclo[5.2.1.0 2,6]decane-8,8-diyl group (10 carbon atoms), a 2,2-adamantylidene group (10 carbon atoms), and a cyclododecanylidene group (12 carbon atoms). Preferred are a cyclohexylidene group (6 carbon atoms), a 3-methylcyclohexylidene group (7 carbon atoms), a 4-methylcyclohexylidene group (7 carbon atoms), a 3,3,5-trimethylcyclohexylidene group (9 carbon atoms), and a cyclododecanylidene group (12 carbon atoms), more preferred are a cyclohexylidene group (6 carbon atoms), a 3,3,5-trimethylcyclohexylidene group (9 carbon atoms), and a cyclododecanylidene group (12 carbon atoms), and particularly preferred are a cyclohexylidene group (6 carbon atoms) and a 3,3,5-trimethylcyclohexylidene group (9 carbon atoms).

When X in general formula (1) is represented by general formula (1b), $Ar_1$ and $Ar_2$ are preferably each independently a benzene ring or a naphthalene ring, and $Ar_1$ and $Ar_2$ are more preferably each a benzene ring. For example, when $Ar_1$ and $Ar_2$ are each a benzene ring, the group represented by general formula (1b) is a fluorenylidene group.

The position of bonding of X in general formula (1) to the two benzoxazine rings is preferably the ortho or para position on the benzene ring relative to the oxygen atom of each benzoxazine ring.

As specific examples of the novel benzoxazine compound represented by general formula (1) in the present invention, compounds (p-1) to (p-126) having the following chemical structures are shown. Of these, compounds (p-1) to (p-63) are preferred, compounds (p-1) to (p-42), compounds (p-46) to (p-48), and compounds (p-52) to (p-63) are more preferred, and compounds (p-1) to (p-15), compounds (p-22) to (p-30), compounds (p-34) to (p-42), and compounds (p-52) to (p-63) are still more preferred.

[Chem. 6]

(p-1)

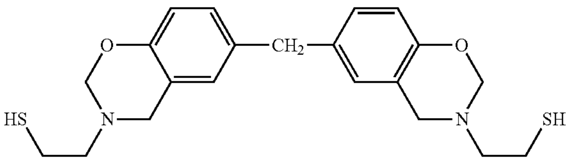

(p-2)

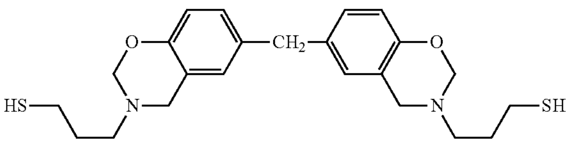

(p-3)

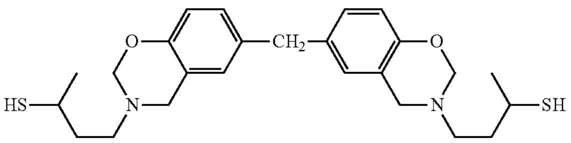

(p-4)

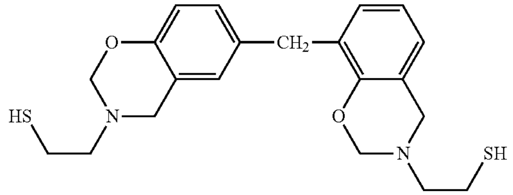

(p-5)

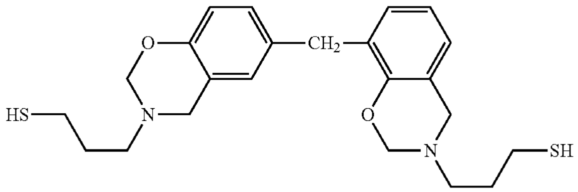

(p-6)

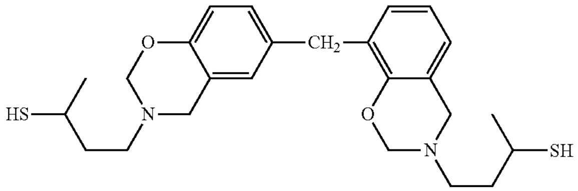

(p-7)

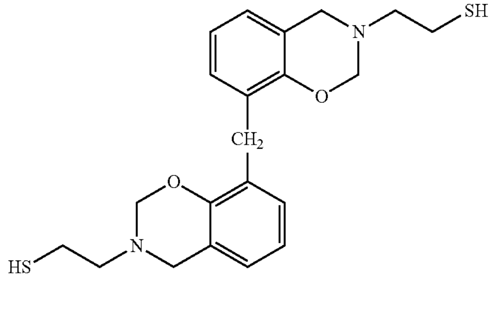

-continued
(p-8)
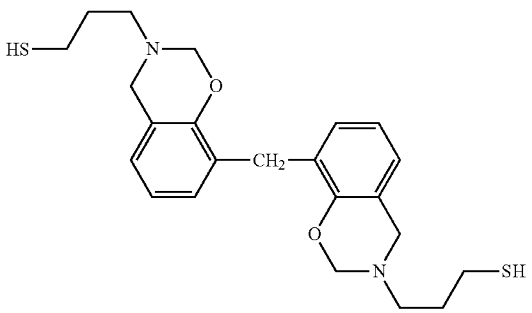
(p-9)
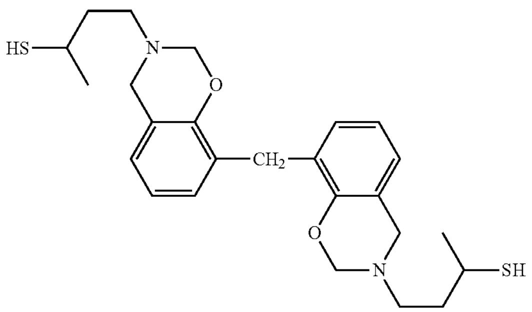
(p-10)
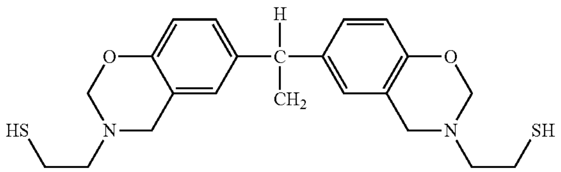
(p-11)
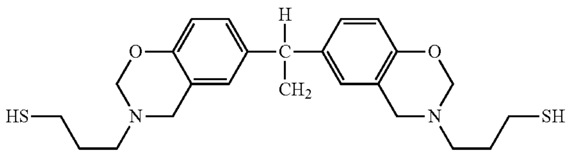
(p-12)
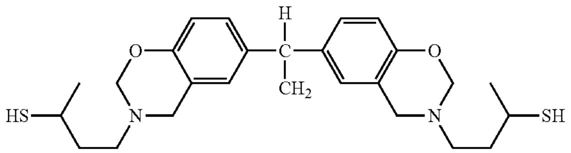
[Chem. 7]
(p-13)
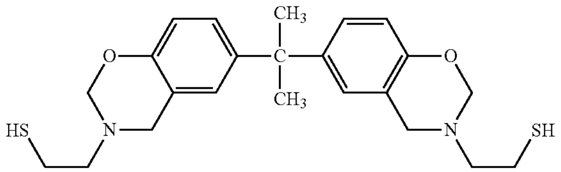
(p-14)
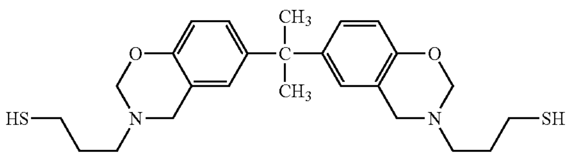
-continued
(p-15)
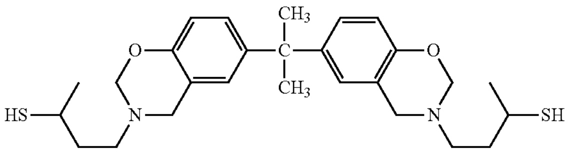
(p-16)
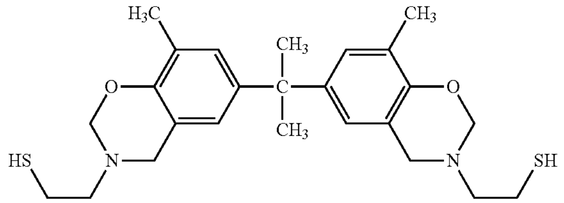
(p-17)
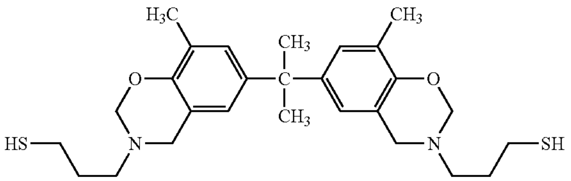
(p-18)
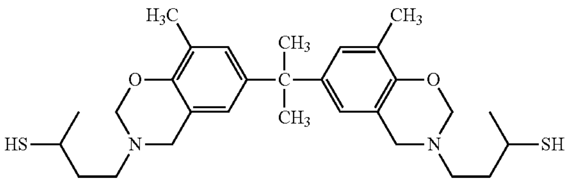
(p-19)
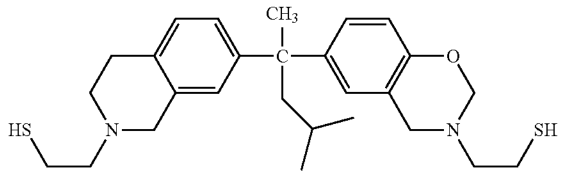
(p-20)
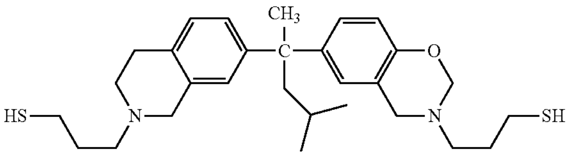
(p-21)
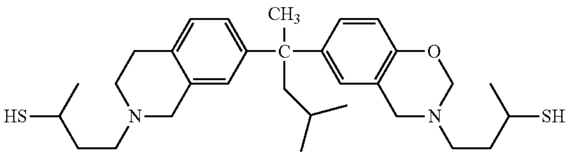
(p-22)
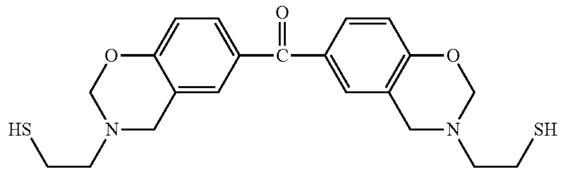

-continued
(p-23)
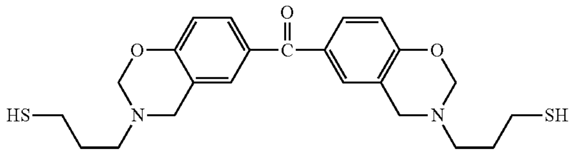
(p-24)
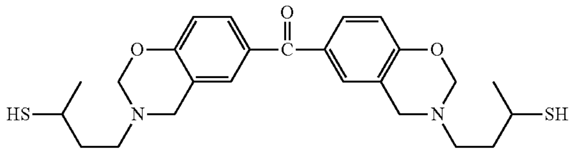
[Chem. 8]
(p-25)
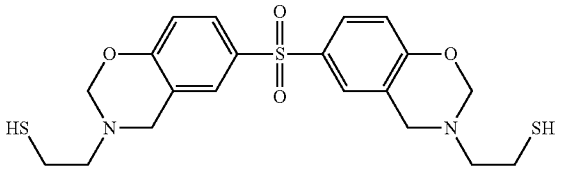
(p-26)
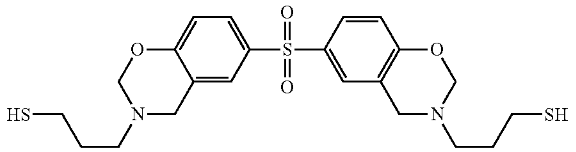
(p-27)
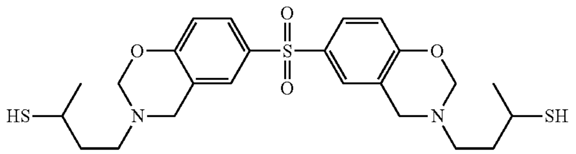
(p-28)
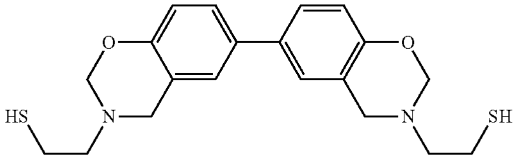
(p-29)
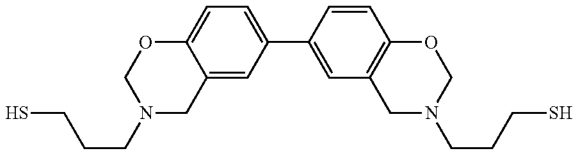
(p-30)
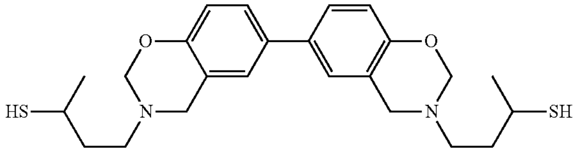
-continued
(p-31)
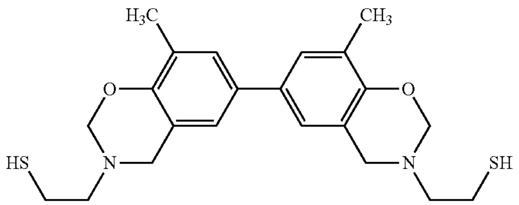
(p-32)
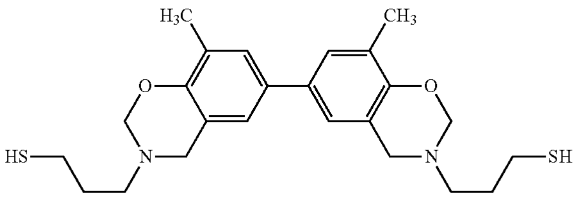
(p-33)
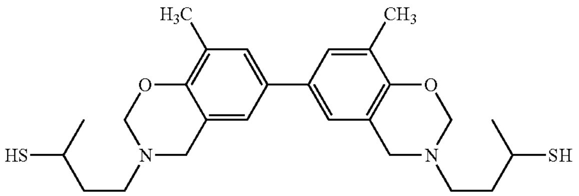
(p-34)
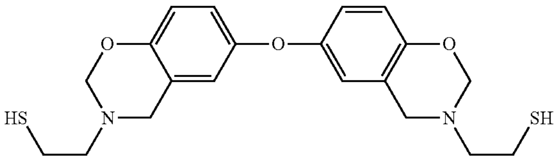
(p-35)
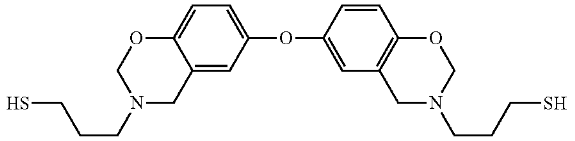
(p-36)
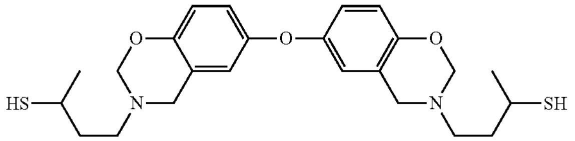
[Chem. 9]
(p-37)
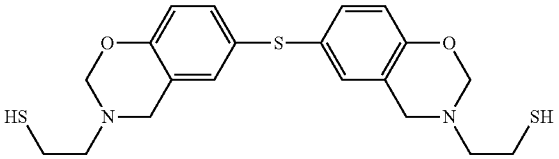
(p-38)
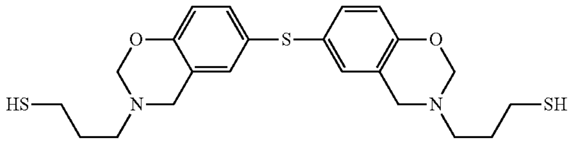

-continued
(p-39)
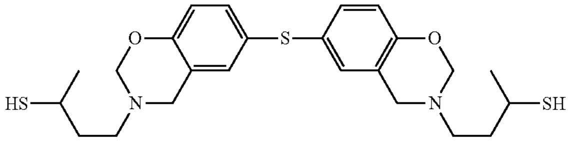
(p-40)
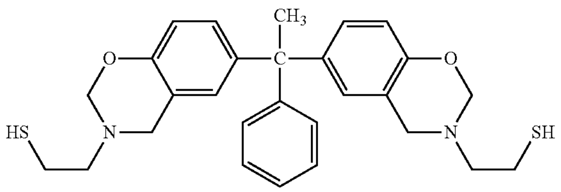
(p-41)
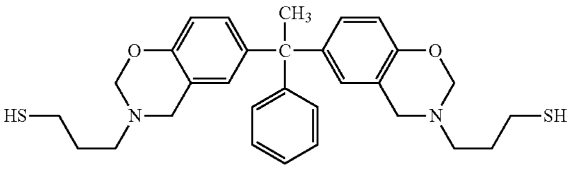
(p-42)
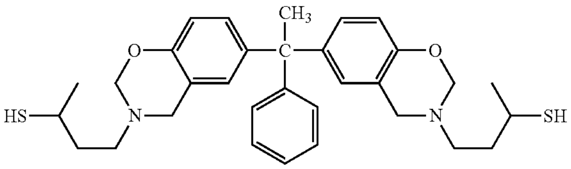
(p-43)
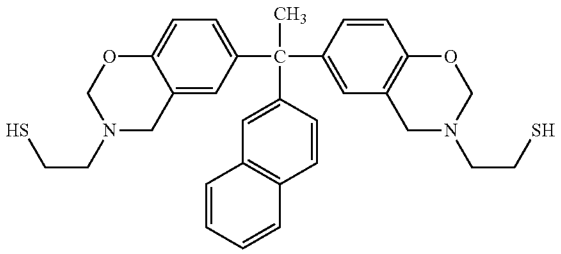
(p-44)
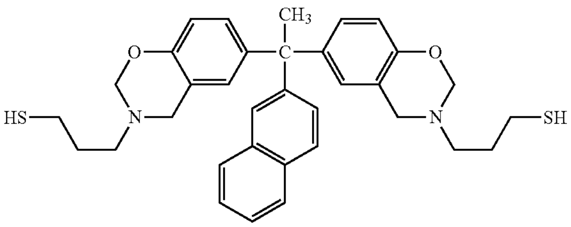
(p-45)
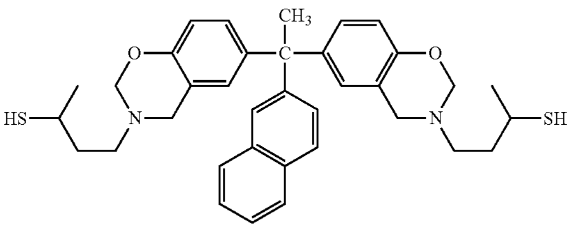
-continued
(p-46)
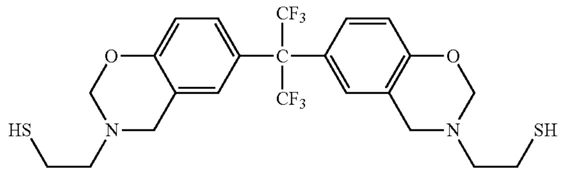
(p-47)
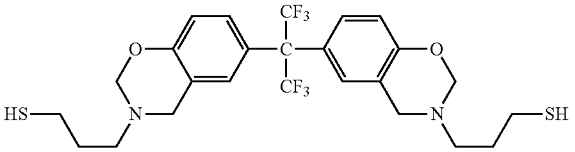
(p-48)
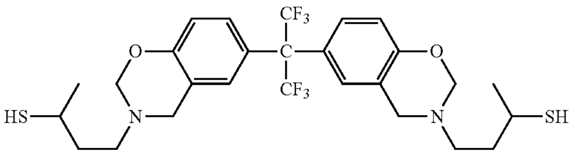
[Chem. 10]
(p-49)
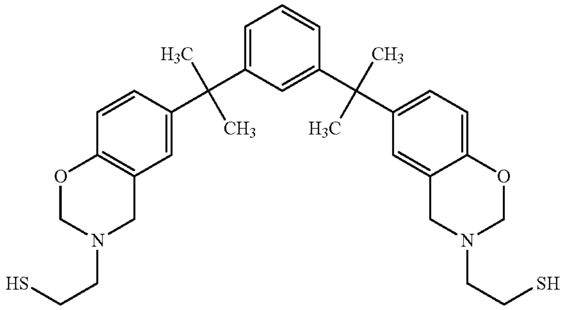
(p-50)
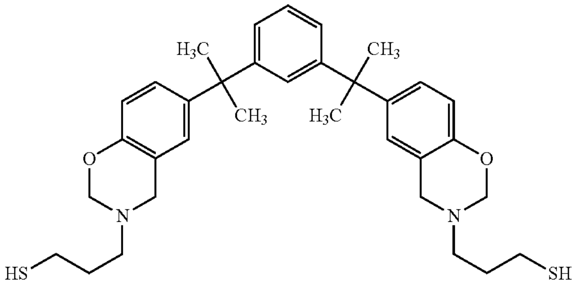
(p-51)
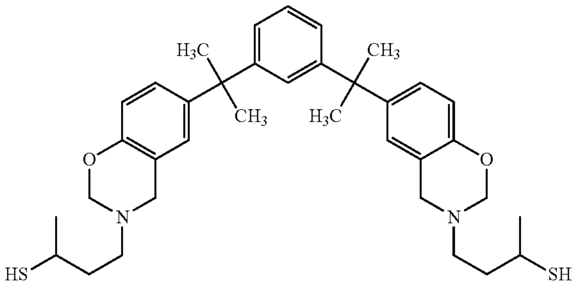

-continued
(p-52)
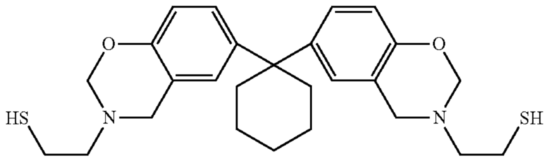
(p-53)
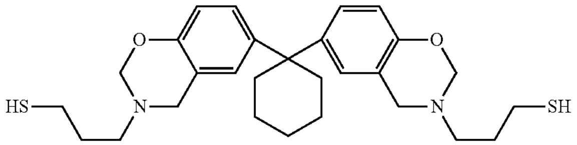
(p-54)
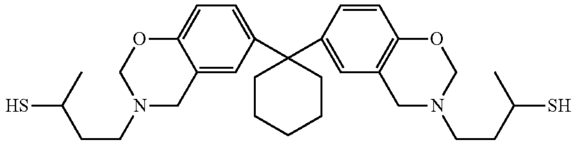
(p-55)
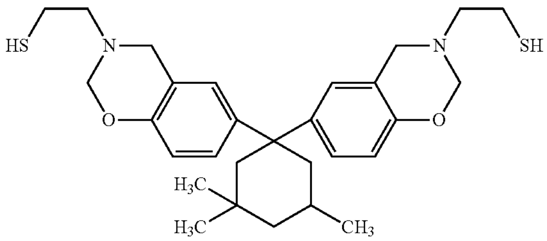
(p-56)
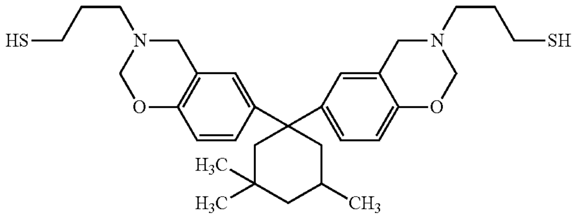
(p-57)
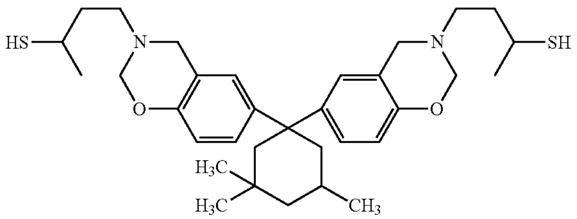
(p-58)
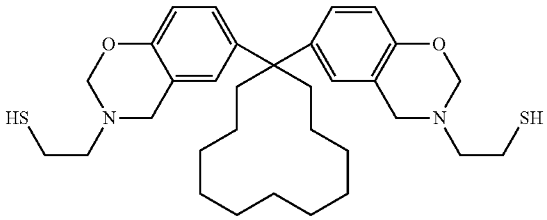
-continued
(p-59)
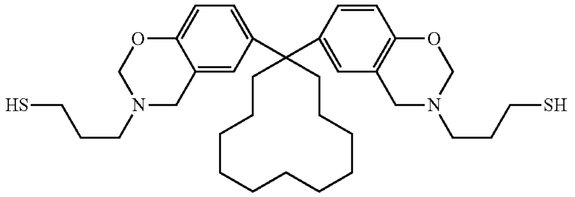
(p-60)
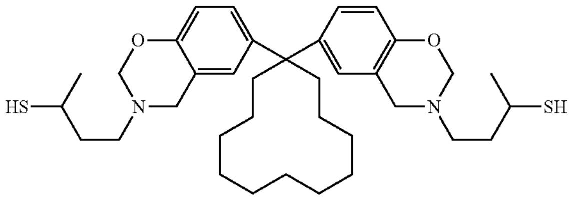
(p-61)
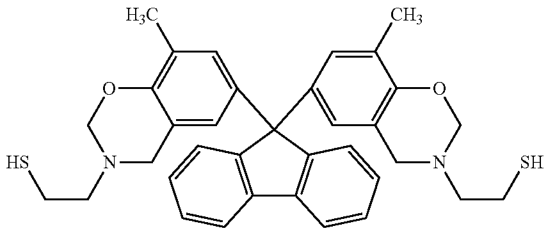
(p-62)
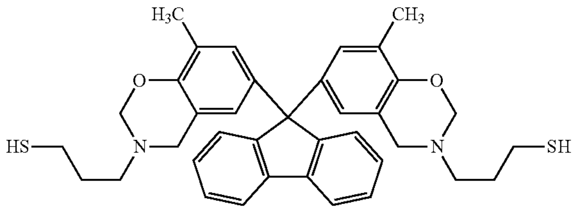
(p-63)
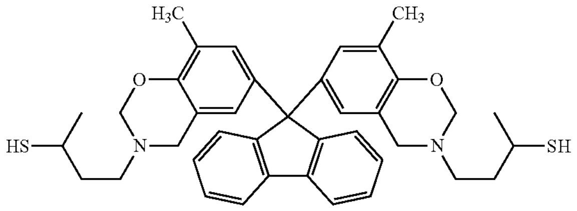
(p-64)
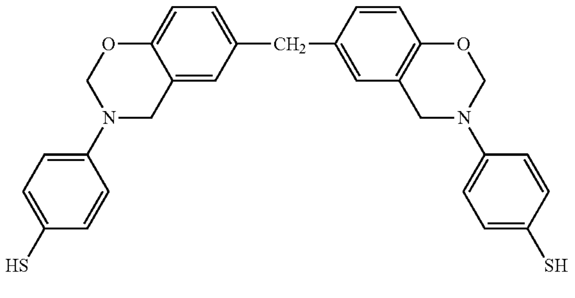

-continued
(p-65)
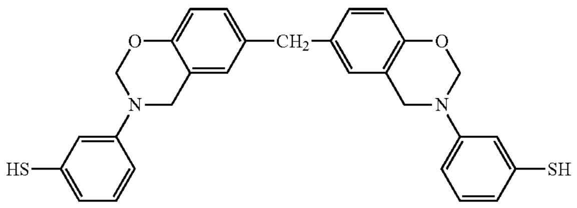
(p-66)
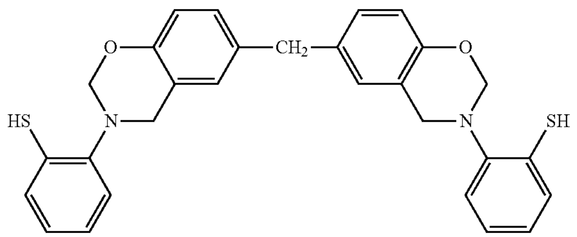
(p-67)
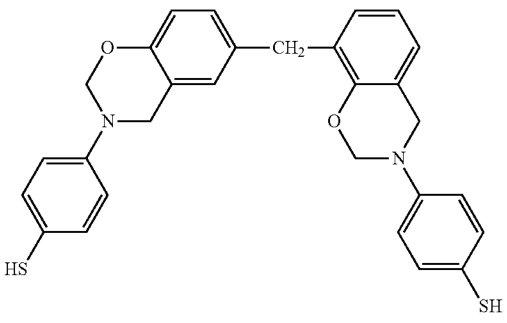
(p-68)
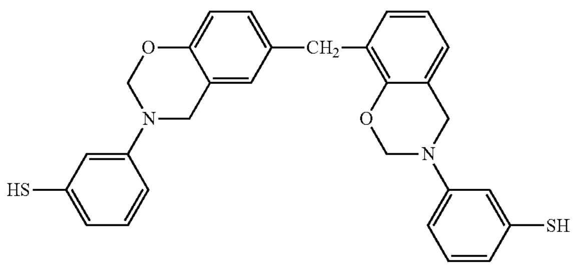
(p-69)
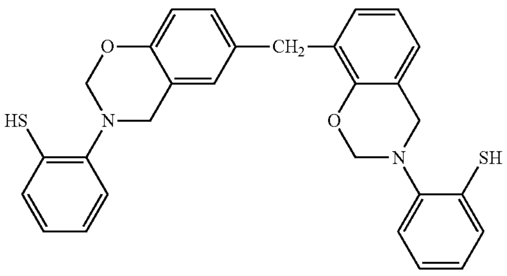
-continued
[Chem. 12]
(p-70)
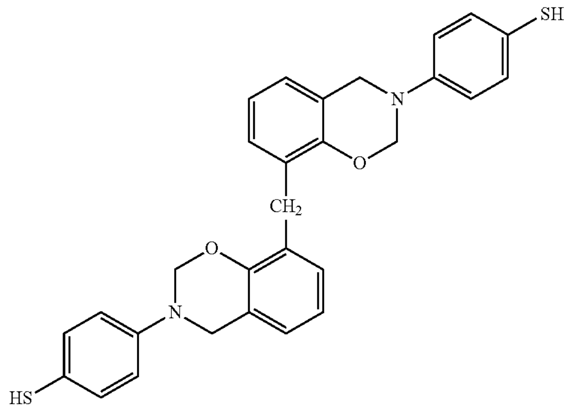
(p-71)
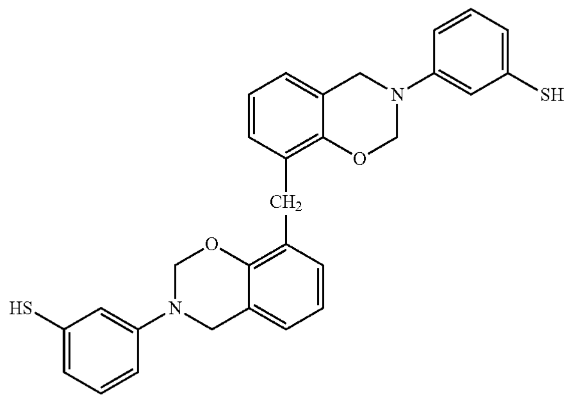
(p-72)
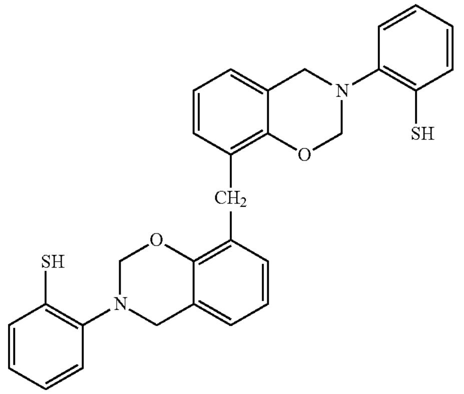
(p-73)
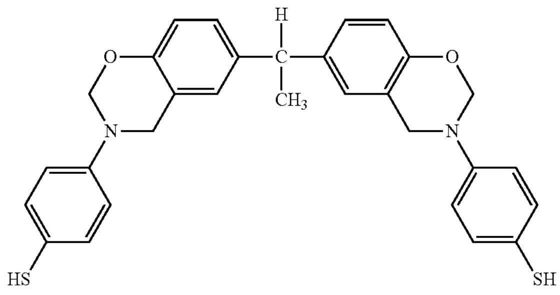

-continued
(p-74)
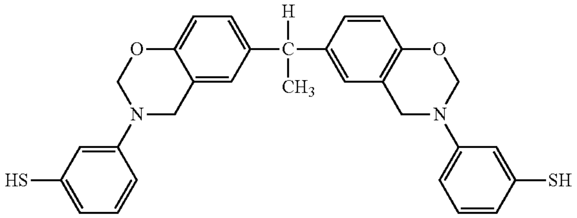
(p-75)
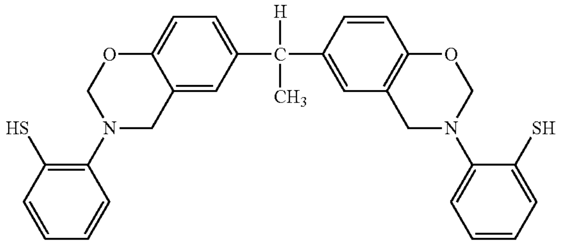
(p-76)
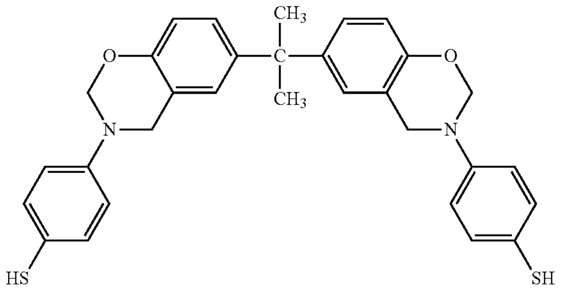
(p-77)
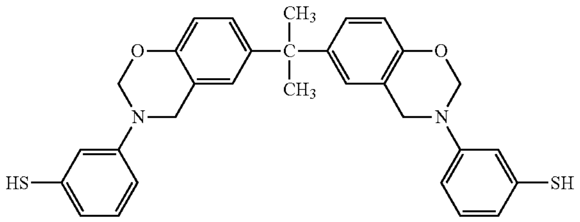
(p-78)
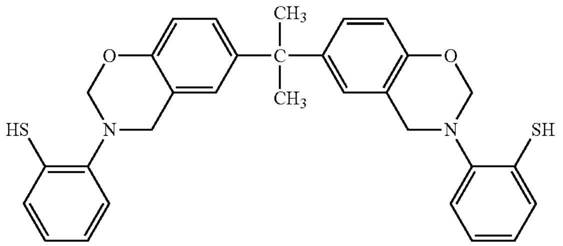
-continued
[Chem. 13]
(p-79)
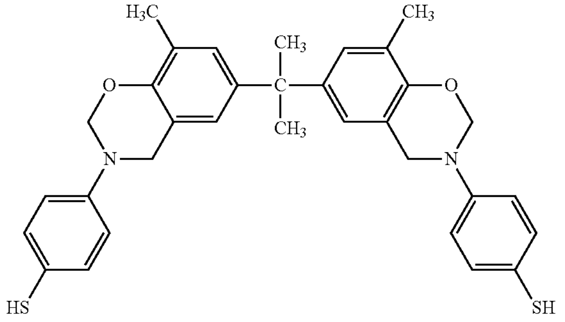
(p-80)
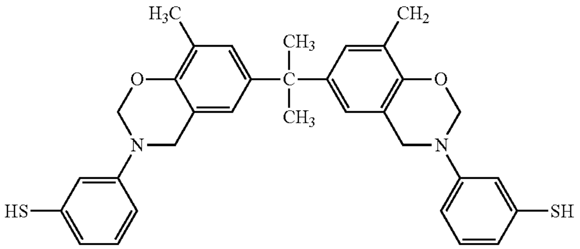
(p-81)
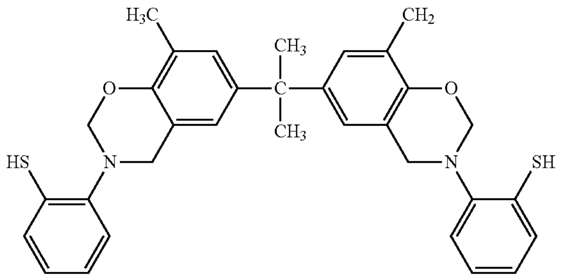
(p-82)
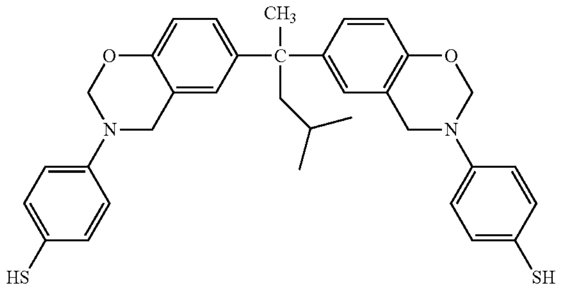
(p-83)
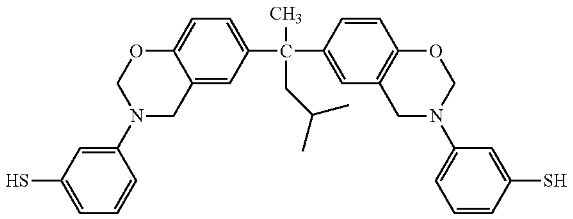

-continued
(p-84)
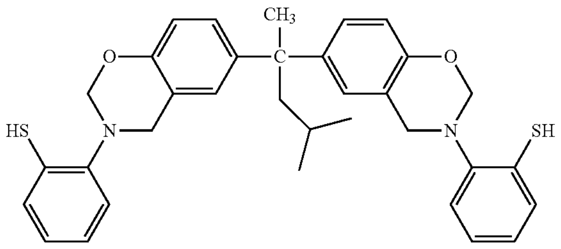
(p-85)
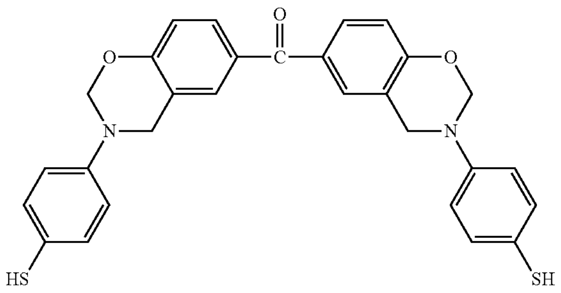
(p-86)
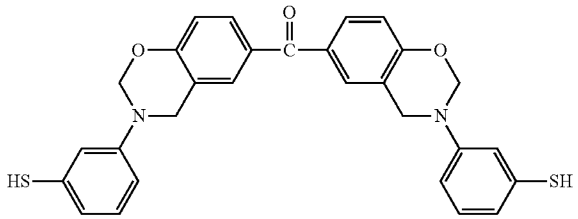
(p-87)
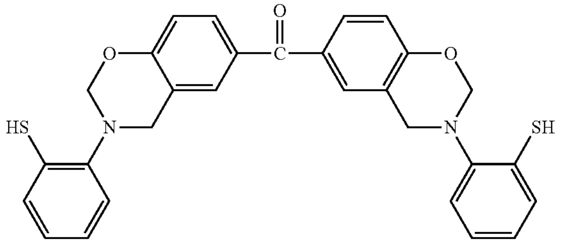
(p-88)
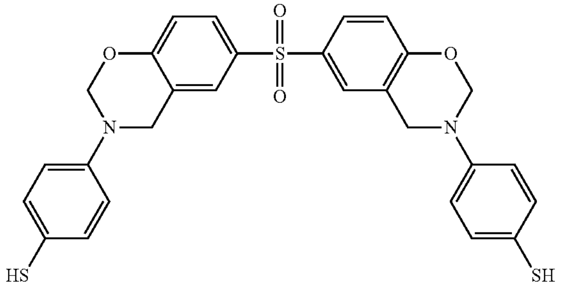
-continued
(p-89)
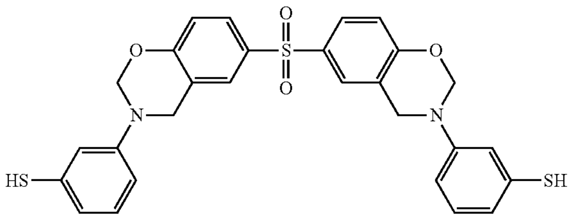
(p-90)
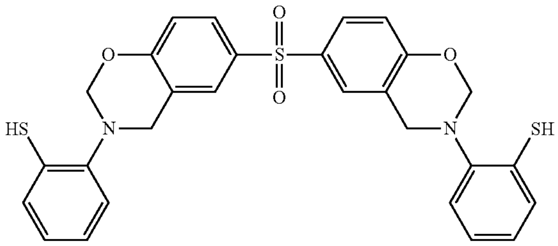
[Chem. 14]
(p-91)
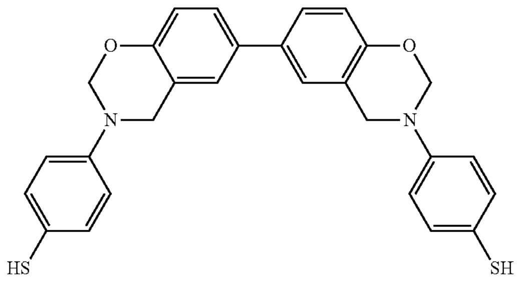
(p-92)
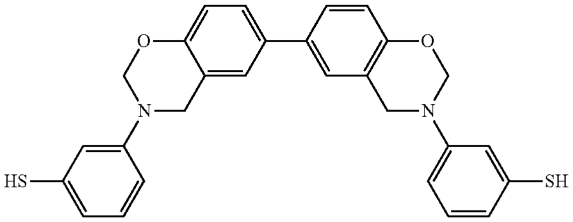
(p-93)
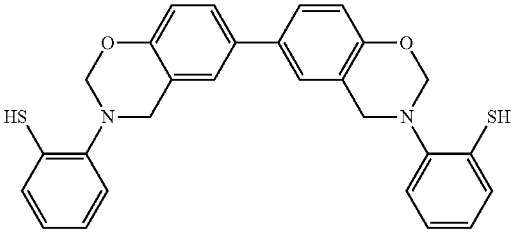

-continued
(p-94)
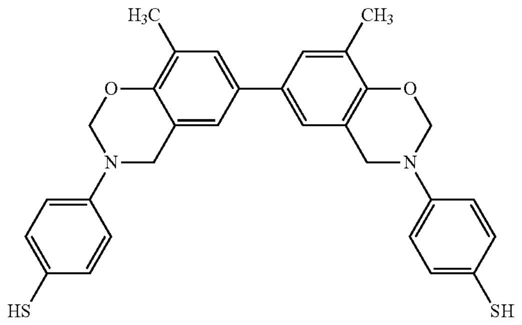
(p-95)
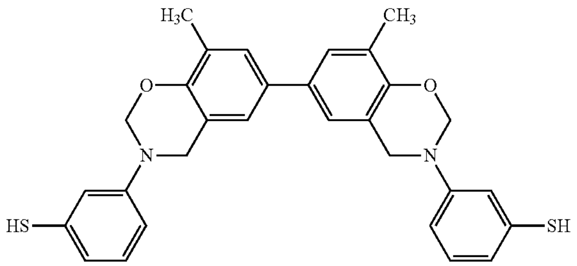
(p-96)
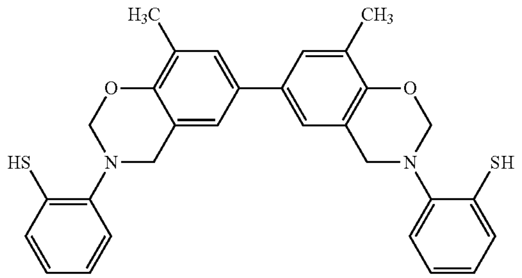
(p-97)
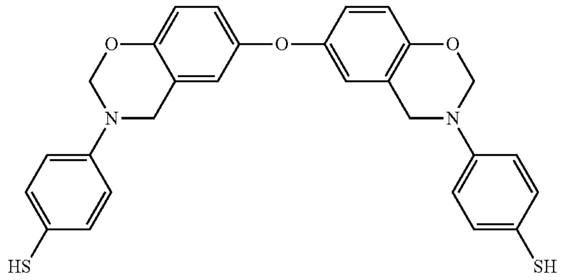
(p-98)
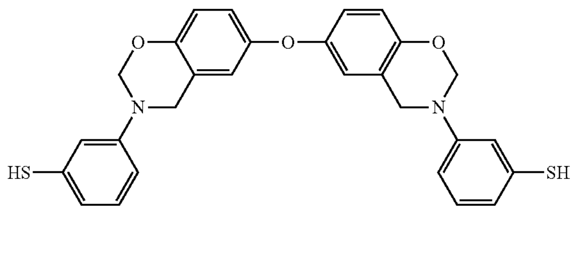
-continued
(p-99)
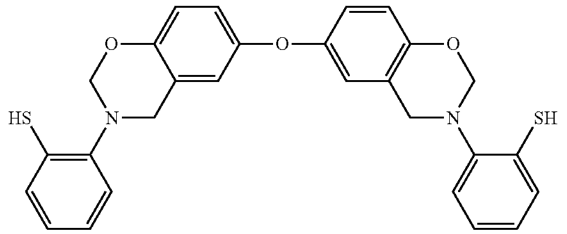
(p-100)
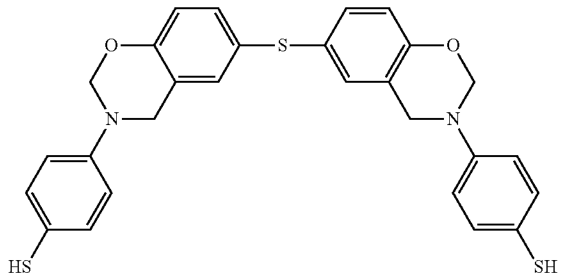
(p-101)
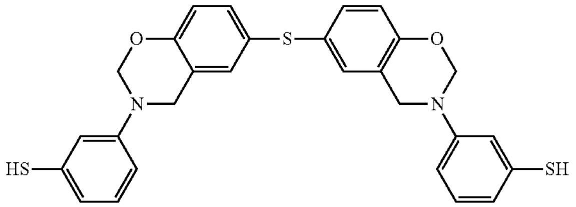
(p-102)
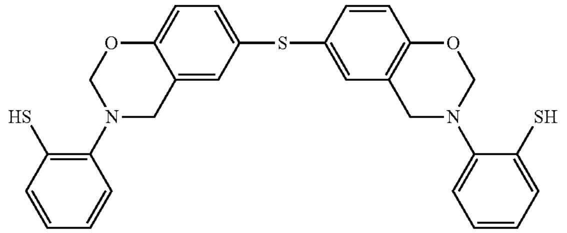
[Chem. 15]
(p-103)
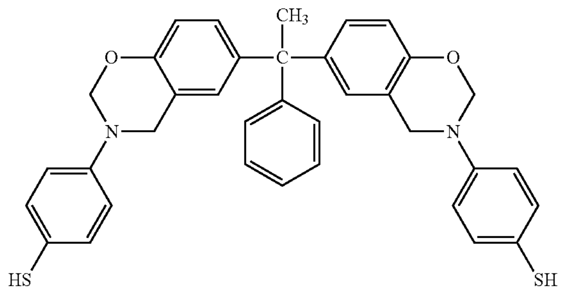
(p-104)
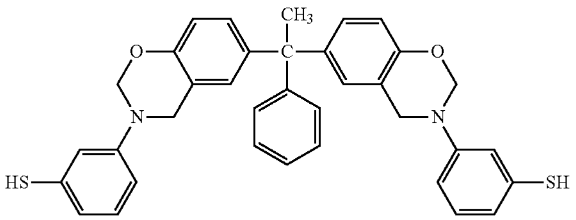

-continued
(p-105)
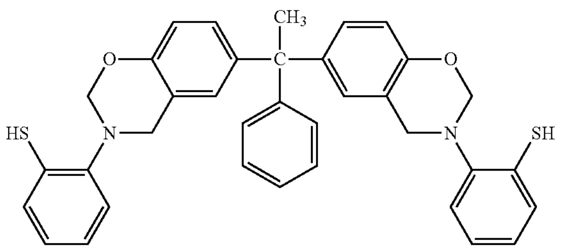
(p-106)
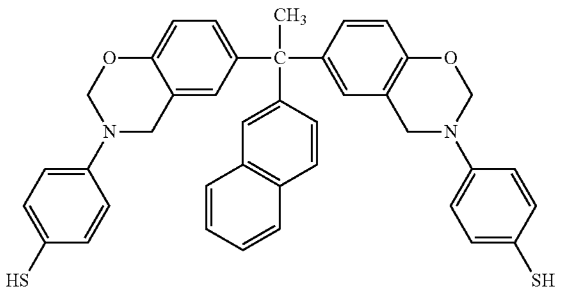
(p-107)
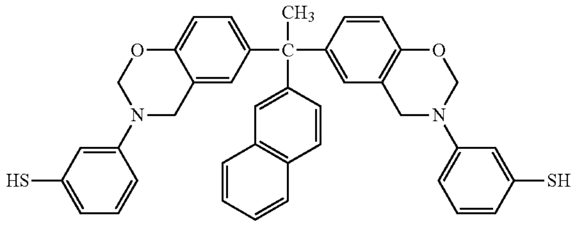
(p-108)
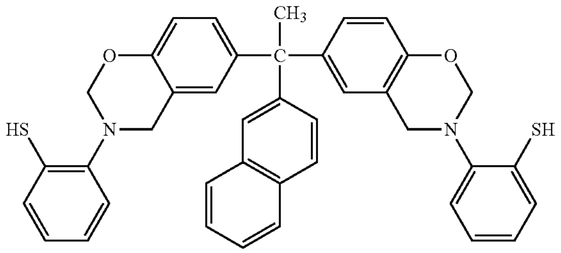
(p-109)
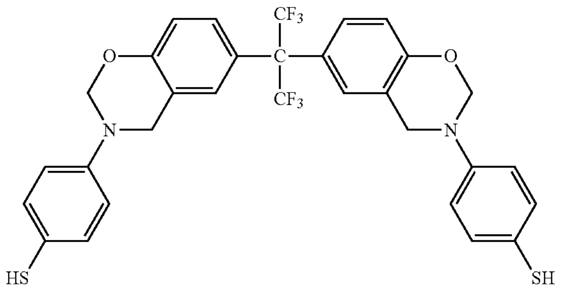
-continued
(p-110)
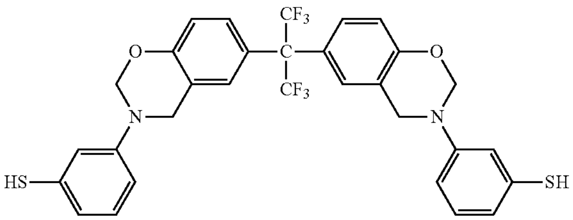
(p-111)
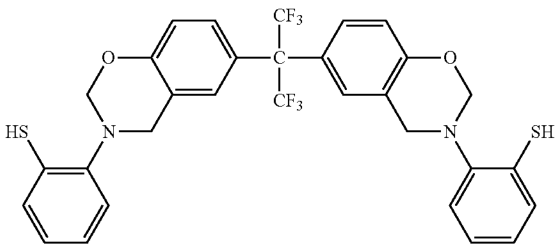
(p-112)
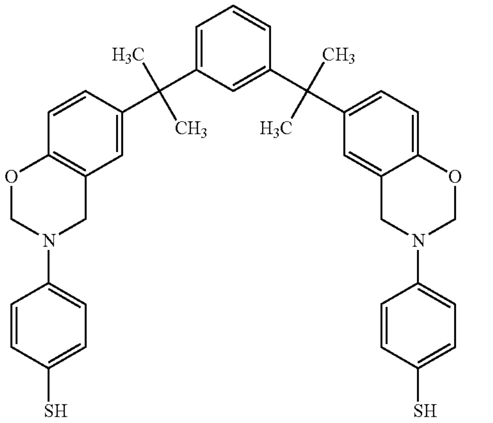
(p-113)
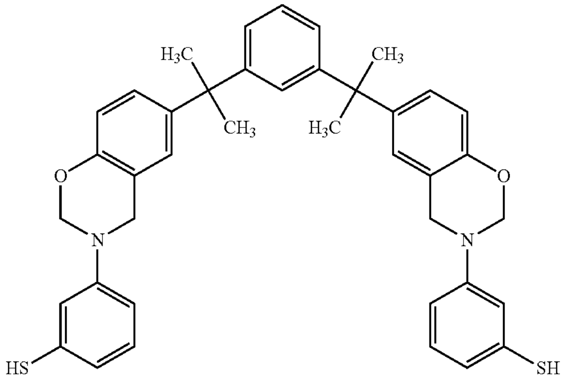

-continued
(p-114)
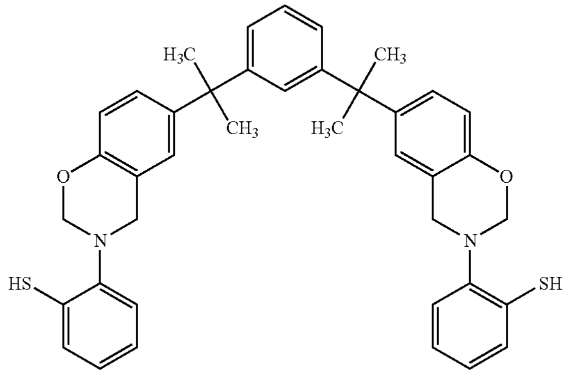
[Chem. 16]
(p-115)
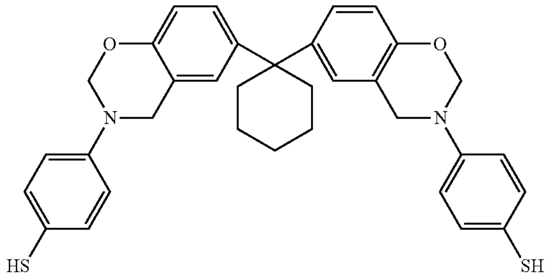
(p-116)
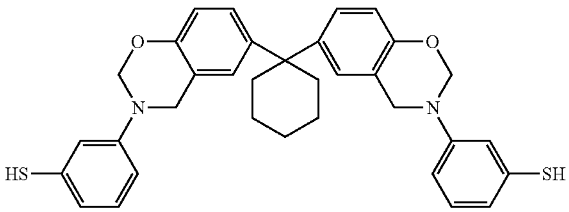
(p-117)
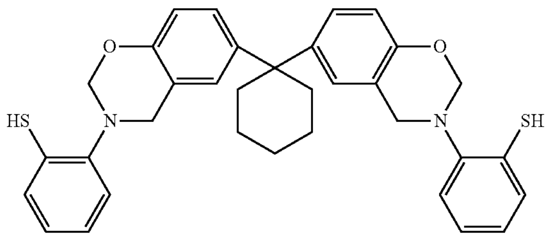
(p-118)
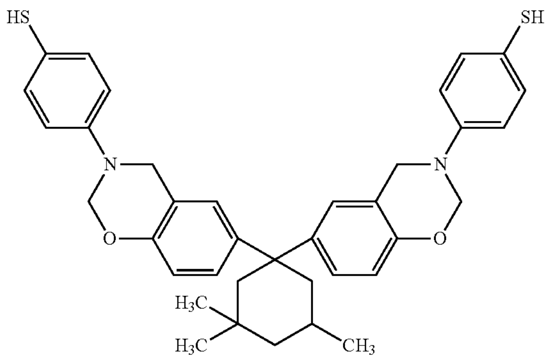
-continued
(p-119)
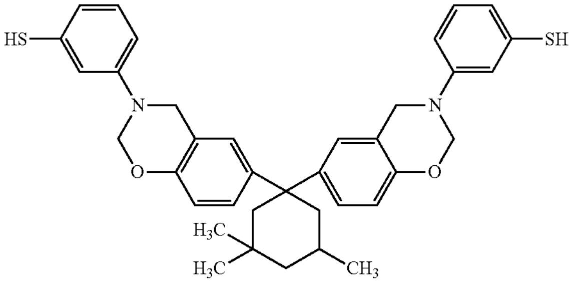
(p-120)
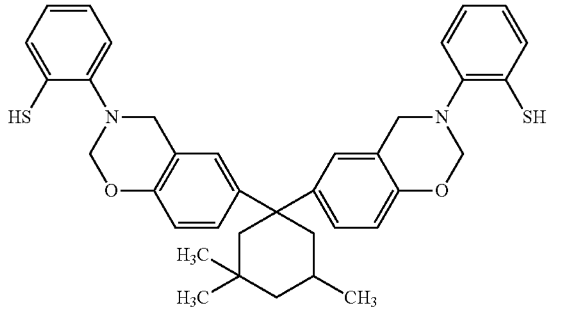
(p-121)
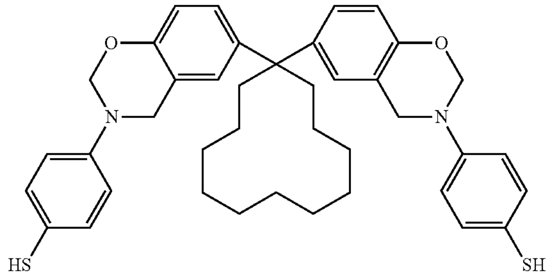
(p-122)
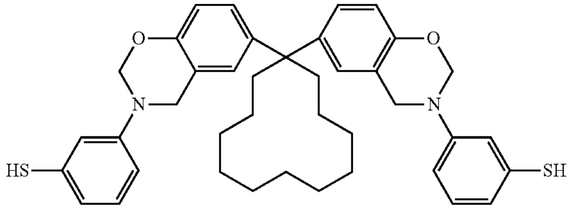
(p-123)
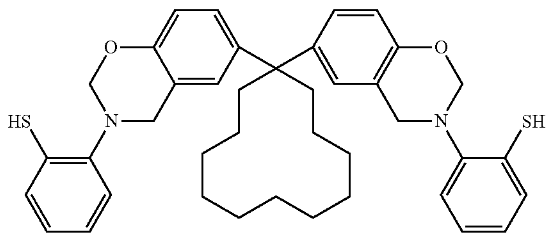

-continued (p-124)

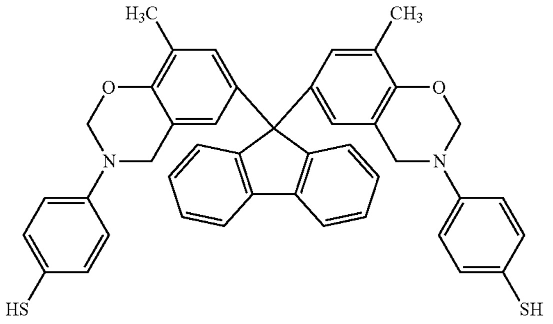

(p-125)

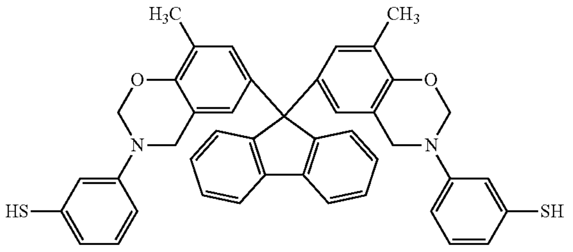

(p-126)

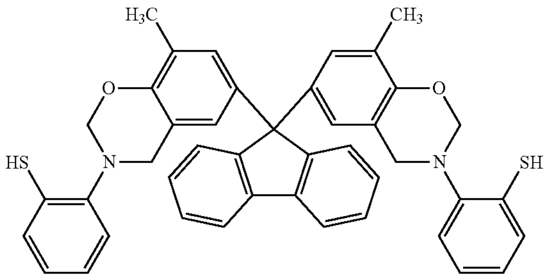

<Method for Producing Inventive Compound>

For the novel benzoxazine compound represented by general formula (1) in the present invention, there are no particular limitations on the starting materials in the production of the benzoxazine compound and the method for producing the benzoxazine compound. For example, as illustrated by the following reaction formula, a production method in which a bisphenol compound represented by general formula (2), an aminothiol compound represented by general formula (3), and formaldehyde are allowed to undergo dehydration condensation reaction to cyclize, thereby obtaining the target novel benzoxazine compound represented by general formula (1), may be used.

[Chem. 17]

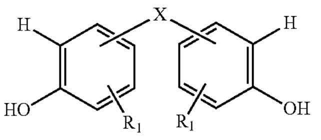

(2)

+ 2 $H_2N—R_2—SH$ +

(3)

4 HCHO →

-continued

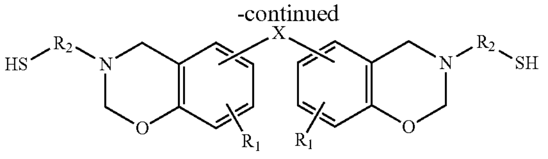

+

(1)

4 $H_2O$ (In the formula, $R_1$, $R_2$, and X represent the same as in general formula (1).)

In the above production method, a bisphenol compound represented by general formula (2), an aminothiol compound represented by general formula (3), and a formaldehyde are used as starting materials.

Specific examples of the bisphenol compound represented by general formula (2) include bisphenol F (bis(2-hydroxyphenyl)methane, 2-hydroxyphenyl-4-hydroxyphenylmethane, bis(4-hydroxyphenyl)methane), bisphenol E (1,1-bis(4-hydroxyphenyl)ethane), bisphenol A (2,2-bis(4-hydroxyphenyl)propane), bisphenol C (2,2-bis(4-hydroxy-3-methylphenyl)propane), 2,2-bis(4-hydroxyphenyl)-4-methylpentane, 4,4'-dihydroxybiphenyl, 4,4'-dihydroxy-3,3'-dimethylbiphenyl, bis(4-hydroxyphenyl) ether, 4,4'-dihydroxybenzophenone, bis(4-hydroxyphenyl)sulfone, bis (4-hydroxyphenyl) sulfide, 1,1-bis(4-hydroxyphenyl)-1-phenylethane, 1,1-bis(4-hydroxyphenyl)-1-naphthylethane, 2,2-bis(4-hydroxyphenyl)hexafluoropropane, bisphenol M (1,3-bis(2-(4-hydroxyphenyl)-2-propyl)benzene), bisphenol Z (1,1-bis(4-hydroxyphenyl)cyclohexane), bisphenol TMC (1,1-bis(4-hydroxyphenyl)-3,3,5-trimethylcyclohexane), 1,1-bis(4-hydroxyphenyl)cyclododecane, 2,2-bis(4-hydroxyphenyl)adamantane, and 9,9-bis(4-hydroxy-3-methylphenyl)fluorene.

Specific examples of the aminothiol compound represented by general formula (3) include 2-aminoethanethiol, 3-amino-1-propanethiol, 2-amino-1-methylethanethiol, 2-amino-2-methylethanethiol, 5-amino-1-pentanethiol, 6-amino-1-hexanethiol, 2-aminothiophenol, 3-aminothiophenol, 4-aminothiophenol, and 4-aminobenzyl mercaptan. Of these, 2-aminoethanethiol, 3-amino-1-propanethiol, 2-amino-1-methylethanethiol, 2-amino-2-methylethanethiol, 5-amino-1-pentanethiol, and 6-amino-1-hexanethiol are preferred, 2-aminoethanethiol, 3-amino-1-propanethiol, and 2-amino-1-methylethanethiol are more preferred, and 2-aminoethanethiol is particularly preferred.

Specific examples of the formaldehyde include an aqueous formaldehyde solution, 1,3,5-trioxane, and paraformaldehyde.

In the above production method, the amount of the formaldehyde used is preferably in the range of 4.0 to 20.0 mol, more preferably in the range of 4.0 to 16.0 mol, still more preferably in the range of 4.0 to 12.0 mol, relative to 1 mol of the bisphenol compound represented by general formula (2).

In the above production method, the amount of the aminothiol compound represented by general formula (3) used is preferably in the range of 2.0 to 10.0 mol, more preferably in the range of 2.0 to 8.0 mol, still more preferably in the range of 2.0 to 6.0 mol, relative to 1 mol of the bisphenol compound represented by general formula (2).

A catalyst for accelerating the reaction is not particularly necessary, but an acid catalyst or a base catalyst can be used as needed. In this case, examples of acid catalysts that can be used include, but are not limited to, concentrated hydrochloric acid, hydrochloric acid gas, trifluoroacetic acid, methanesulfonic acid, p-toluenesulfonic acid, benzoic acid, and mixtures thereof, and examples of base catalysts that can be used include, but are not limited to, sodium hydroxide, sodium carbonate, triethylamine, triethanolamine, and mixtures thereof.

The reaction is typically performed in the presence of a solvent. The solvent is not particularly limited as long as it does not inhibit the reaction, and preferred examples include toluene, xylene, ethyl acetate, butyl acetate, chloroform, dichloromethane, tetrahydrofuran, and dioxane. These solvents can be used alone or in combination. The amount of solvent used is not particularly limited as long as the reaction is not hindered, and is typically in the range of 0.5 to 5 times, preferably in the range of 1 to 3 times the amount of the bisphenol compound represented by general formula (2) on a weight basis.

The reaction temperature is typically in the range of 10° C. to 150° C., preferably in the range of 10° C. to 120° C., more preferably in the range of 10° C. to 80° C., still more preferably in the range of 20° C. to 70° C., particularly preferably in the range of 20° C. to 60° C.

The reaction may be performed under normal pressure conditions, or may be performed under increased pressure or reduced pressure.

In another embodiment, a process of removing water derived from the raw materials or water generated during the reaction out of the system may be included. The process of removing water generated from a reaction solution is not particularly limited and can be performed by distilling the generated water azeotropically with the solvent system in the reaction solution. The generated water can be removed out of the reaction system by using, for example, an isobaric dropping funnel equipped with a cock, a Dimroth condenser, or a Dean-Stark apparatus.

From the final reaction mixture obtained, the benzoxazine compound represented by general formula (1) can be obtained by a known method after completion of the reaction. For example, after the reaction, the remaining raw materials and solvent may be distilled off from the reaction mixture to thereby obtain the target as a residual liquid. Other possible methods include adding the residual liquid to a poor solvent to obtain the target as a precipitate, and adding a solvent to the reaction mixture to cause crystallization and performing filtration to obtain the target as powder or particles. The benzoxazine compound collected by any of these methods can be made into a high-purity product by, for example, standard purification means such as washing with a solvent or water or recrystallization.

<Resin Raw Material Composition Containing Benzoxazine Compound Represented by General Formula (1)>

A resin raw material composition according to the present invention contains the benzoxazine compound represented by general formula (1) and can be obtained by distilling off the remaining raw materials and solvent from the reaction mixture described above. Alternatively, the target in the form of a precipitate can be obtained by adding the residual liquid to a poor solvent, or the resin raw material composition according to the present invention in the form of powder or particles can be obtained by adding a solvent to the reaction mixture to cause crystallization and performing filtration. For example, the resin raw material composition according to the present invention having a high content of the benzoxazine compound represented by general formula (1) can be obtained by performing standard purification such as washing with a solvent or water or recrystallization.

The resin raw material composition according to the present invention may be produced using, in the reaction for producing the benzoxazine compound represented by general formula (1), the bisphenol compound represented by general formula (2) composed of a mixture in which the position of the linking group X bonded to the benzene rings varies.

The ratio of compounds in which the position of the linking group X bonded to the benzene rings varies in the bisphenol compound represented by general formula (2) for use is not particularly limited.

Specifically, for example, when bisphenol F is used, a mixture of positional isomers thereof, that is, bis(2-hydroxyphenyl)methane, 2-hydroxyphenyl-4-hydroxyphenylmethane, and bis(4-hydroxyphenyl)methane, can be used, and the ratio thereof is not particularly limited.

Bisphenol F containing a large proportion of bis(2-hydroxyphenyl)methane can be obtained by, for example, the method of Japanese Unexamined Patent Application Publication No. 08-245464, and bisphenol F containing a large proportion of bis(4-hydroxyphenyl)methane can be obtained by, for example, the method of Japanese Unexamined Patent Application Publication No. 06-340565.

When such a mixture of positional isomers of bisphenol F and 2-aminoethanethiol as the aminothiol compound represented by general formula (3) are used to synthesize the benzoxazine compound represented by general formula (1) according to the present invention by the production method described above, a mixture of compounds (p-1), (p-7), and (p-13) can be obtained.

The bisphenol compound represented by general formula (2) for use may contain a polynuclear structure, which is a by-product formed during the production of a bisphenol (binuclear structure), and the content ratio thereof is not particularly limited. The bisphenol (binuclear structure) content is preferably 50 wt % or more, more preferably 70 wt % or more, still more preferably 85 wt % or more, particularly preferably 89 wt % or more.

The resin raw material composition in the present invention may contain a compound formed as a by-product in the reaction for producing the benzoxazine compound represented by general formula (1). The by-product may be, for example, a compound having a molecular weight higher than that of the benzoxazine compound represented by general formula (1).

In the resin raw material composition according to the present invention, the content of the benzoxazine compound represented by general formula (1) is not particularly limited. The content can be analyzed by gel permeation chromatography using a differential refractometer as a detector and is typically 10 to 100 area %, preferably 20 to 100 area %, more preferably 30 to 100 area %, particularly preferably 40 to 100 area %, relative to the area of all peaks detected in the analysis.

<Curable Resin Composition that Contains Benzoxazine Compound Represented by General Formula (1) or Resin Raw Material Composition Containing Benzoxazine Compound>

The benzoxazine compound represented by general formula (1) or the resin raw material composition containing the benzoxazine compound according to the present invention can be used in the form of a curable resin composition containing the benzoxazine compound or the resin raw material composition as an essential component.

Examples of such forms include curable resin compositions obtained by mixing the benzoxazine compound represented by general formula (1) or the resin raw material composition containing the benzoxazine compound, with inorganic filler such as silicon oxide, aluminum oxide, magnesium oxide, boron nitride, aluminum nitride, silicon nitride, silicon carbide, or hexagonal boron nitride, or with a reinforcement fiber such as carbon fiber, glass fiber, organic fiber, boron fiber, steel fiber, or aramid fiber.

Examples of other forms include curable resin compositions that contain, as an essential component, the benzoxazine compound represented by general formula (1) or the resin raw material composition containing the benzoxazine compound and contain other polymeric materials.

The polymeric materials constituting the curable resin composition according to the present invention are not particularly limited, and raw materials of an epoxy resin, a phenol resin, a bismaleimide compound, and a benzoxazine compound other than the benzoxazine compound represented by general formula (1) can be contained.

Examples of the epoxy resin include ortho-cresol epoxy resins, biphenyl epoxy resins, biphenyl aralkyl epoxy resins, naphthalene epoxy resins, anthracene dihydride epoxy resins, and brominated novolac epoxy resins.

Examples of the phenol resin include novolac phenol resins such as phenol novolac resin, cresol novolac resin, naphthol novolac resin, aminotriazine novolac resin, and trisphenylmethane phenol novolac resin; modified phenol resins such as terpene-modified phenol resin and dicyclopentadiene-modified phenol resin; aralkyl resins such as phenol aralkyl resins having a phenylene backbone and/or a biphenylene backbone and naphthol aralkyl resins having a phenylene backbone and/or a biphenylene backbone; and resol phenol resins.

Examples of the bismaleimide compound include raw materials of the bismaleimide compound having the following structures.

[Chem. 18]

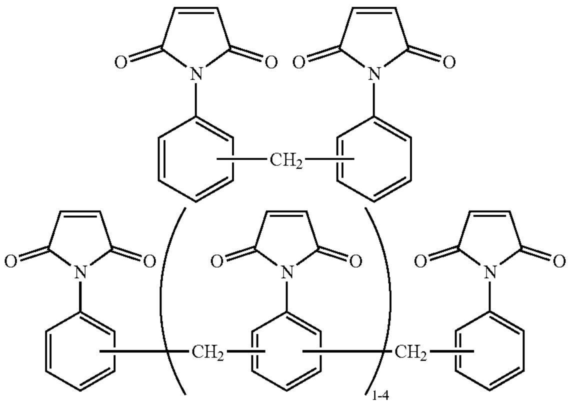

Examples of benzoxazine compounds other than the benzoxazine compound represented by general formula (1) include benzoxazine compounds having structures represented by general formulae (A) to (C).

[Chem. 19]

(A)

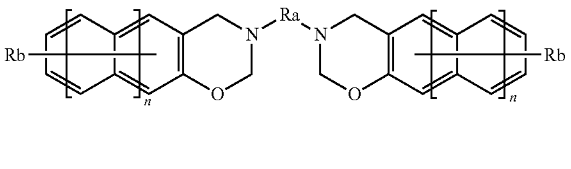

(In the formula, Ra represents a divalent group having 1 to 30 carbon atoms, each Rb independently represents an optionally substituted monovalent group having 1 to 10 carbon atoms, and n represents 0 or 1.)

[Chem. 20]

(B)

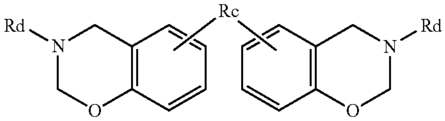

(In the formula, Rc represents a divalent group having 1 to 30 carbon atoms, a direct bond, an oxygen atom, a sulfur atom, a carbonyl group, or a sulfonyl group, and each Rd independently represents a monovalent group having 1 to 10 carbon atoms.)

[Chem. 21]

(C)

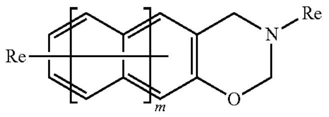

(In the formula, each Re independently represents a monovalent group having 1 to 10 carbon atoms, and m represents 0 or 1.)

Ra in the benzoxazine compound having the structure represented by general formula (A) represents a divalent group having 1 to 30 carbon atoms. Specific examples thereof include alkylene groups such as 1,2-ethylene, 1,4-butylene, and 1,6-hexylene; alkylene groups having a cyclic structure, such as 1,4-cyclohexylene, dicyclopentadienylene, and adamantylene; and arylene groups such as 1,4-phenylene, 4,4'-biphenylene, diphenyl ether-4,4'-diyl, diphenyl ether-3,4'-diyl, diphenyl ketone-4,4'-diyl, and diphenyl sulfone-4,4'-diyl.

Each Rb in the benzoxazine compound having the structure represented by general formula (A) independently represents a monovalent group having 1 to 10 carbon atoms. Specific examples thereof include alkyl groups such as a methyl group, an ethyl group, a propyl group, and a butyl group; alkenyl groups such as a vinyl group and an allyl group; alkynyl groups such as an ethynyl group and a propargyl group; and aryl groups such as a phenyl group and a naphthyl group, and these groups may further have a substituent such as an alkoxy group having 1 to 4 carbon atoms, an acyl group having 1 to 4 carbon atoms, a halogen atom, a carboxyl group, a sulfo group, an allyloxy group, a hydroxy group, or a thiol group.

Examples of the benzoxazine compound having the structure represented by general formula (A) include P-d type benzoxazine manufactured by Shikoku Chemicals Corporation, and JBZ-OP100N and JBZ-BP100N manufactured by JFE Chemical Corporation.

Rc in the benzoxazine compound having the structure represented by general formula (B) represents a divalent group having 1 to 30 carbon atoms, a direct bond, an oxygen atom, a sulfur atom, a carbonyl group, or a sulfonyl group. Examples of the divalent group having 1 to 30 carbon atoms include alkylene groups such as methylene, 1,2-ethylene, 1,4-butylene, and 1,6-hexylene; alkylene groups having a cyclic structure, such as 1,4-cyclohexylene, dicyclopentadienylene, and adamantylene; and alkylidene groups such as ethylidene, propylidene, isopropylidene, butylidene, phenylethylidene, cyclopentylidene, cyclohexylidene, cycloheptylidene, cyclododecylidene, 3,3,5-trimethylcyclohexylidene, and fluorenylidene.

Each Rd in the benzoxazine compound having the structure represented by general formula (B) independently represents a monovalent group having 1 to 10 carbon atoms. Specific examples thereof include alkyl groups such as a methyl group, an ethyl group, a propyl group, and a butyl group; alkenyl groups such as a vinyl group and an allyl group; alkynyl groups such as an ethynyl group and a propargyl group; and aryl groups such as a phenyl group and a naphthyl group, and these substituents may further have a substituent such as an alkoxy group having 1 to 4 carbon atoms, an acyl group having 1 to 4 carbon atoms, a halogen atom, a carboxyl group, a sulfo group, an allyloxy group, or a hydroxy group.

Examples of the benzoxazine compound having the structure represented by general formula (B) include F-a type benzoxazine manufactured by Shikoku Chemicals Corporation and BS-BXZ manufactured by Konishi Chemical Ind. Co., Ltd.

Each Re in the benzoxazine compound having the structure represented by general formula (C) independently represents a monovalent group having 1 to 10 carbon atoms. Specific examples thereof include alkyl groups such as a methyl group, an ethyl group, a propyl group, and a butyl group; alkenyl groups such as a vinyl group and an allyl group; alkynyl groups such as an ethynyl group and a propargyl group; and aryl groups such as a phenyl group and a naphthyl group, and these substituents may further have a substituent such as an alkoxy group having 1 to 4 carbon atoms, an acyl group having 1 to 4 carbon atoms, a halogen atom, a carboxyl group, a sulfo group, an allyloxy group, a hydroxy group, or a thiol group.

In particular, the curable resin composition according to the present invention preferably contains the benzoxazine compound represented by general formula (1) or the resin raw material composition containing the benzoxazine compound, and at least one selected from the group consisting of epoxy resins, benzoxazine compounds other than the benzoxazine compound represented by general formula (1), phenol resins, and bismaleimide compounds.

In the curable resin composition according to the present invention, the amount of the other polymeric materials mixed with the benzoxazine compound represented by general formula (1) or the resin raw material composition containing the benzoxazine compound is in the range of 0.01 parts by weight to 100 parts by weight relative to 1 part by weight of the benzoxazine compound represented by general formula (1) or the resin raw material composition containing the benzoxazine compound.

The curable resin composition according to the present invention can be obtained by adding the benzoxazine compound represented by general formula (1) or the resin raw material composition containing the benzoxazine compound to the other optional polymeric materials described above. The method of the addition is not particularly limited, and a method known in the art can be employed. Examples of the method include addition during synthesis or polymerization of the polymeric materials, addition of a resin formed of the polymeric materials to a molten resin melted in, for example, a melt extrusion step, and infiltration into, for example, a resin product formed of the polymeric materials.

The curable resin composition according to the present invention may entrain bubbles when cured if water or a residual solvent is contained in the composition, and thus to prevent this, it is preferable to perform a vacuum degassing treatment as a pretreatment. The vacuum degassing treatment may be performed at any temperature at which the curable resin composition according to the present invention is in a molten state but is preferably performed at up to 150° C. because curing does not proceed and degassing is facilitated. The vacuum degassing treatment is preferably, but not necessarily, performed at a low pressure (highly reduced pressure) and may be performed either in air or in a nitrogen-purged atmosphere. The vacuum degassing treatment is performed until no bubbles can be visually observed.

The curable resin composition according to the present invention can be used as a mixture with an inorganic filler such as silicon oxide, aluminum oxide, magnesium oxide, boron nitride, aluminum nitride, silicon nitride, silicon carbide, or hexagonal boron nitride, or a reinforcement fiber such as carbon fiber, glass fiber, organic fiber, boron fiber, steel fiber, or aramid fiber depending on the need in the application.

<Cured Product Obtained by Curing Curable Resin Composition According to Present Invention>

Next, a cured product according to the present invention will be described.

The cured product according to the present invention can be obtained by curing the curable resin composition according to the present invention, which contains, as an essential component, the benzoxazine compound represented by general formula (1) or the resin raw material composition containing the benzoxazine compound according to the present invention.

Examples of the method for producing the cured product according to the present invention include curing by heating to a predetermined temperature; melting by heating, injecting into a mold or the like, and further heating the mold to achieve curing and molding; and injecting a melt into a preheated mold and curing the melt.

The cured product according to the present invention can be cured by performing ring-opening polymerization under the same curing conditions as those for ordinary benzoxazines. The curing temperature is typically in a temperature range of 120° C. to 300° C., preferably in a temperature range of 120° C. to 280° C., more preferably in a temperature range of 130° C. to 250° C., and is particularly preferably in a temperature range of 150° C. to 240° C. in order to provide a cured product with improved mechanical properties. When curing is performed in such a temperature range, the reaction time may be about 1 to 10 hours.

The production of the cured product may be performed either in air or in an inert gas atmosphere such as nitrogen, but is preferably performed in an inert gas atmosphere in order to prevent oxygen-induced degradation of the cured product obtained.

The resin composition according to the present invention can be cured by heat alone, but it is preferable to use a curing accelerator depending on, for example, the components other than the benzoxazine compound represented by general formula (1) and the content thereof. Examples of curing accelerators that can be used include, but are not limited to, tertiary amines such as 1,8-diaza-bicyclo[5.4.0]undecene-7, triethylenediamine, and tris(2,4,6-dimethylaminomethyl) phenol; imidazoles such as 2-ethyl-4-methylimidazole and 2-methylimidazole; phosphorus compounds such as triphenylphosphine, tetraphenylphosphonium bromide, tetraphenylphosphonium tetraphenylborate, and tetra-n-butylphosphonium-O,O-diethyl phosphorodithioate; quaternary ammonium salts; organic metal salts; and derivatives thereof. These may be used alone or in combination. Among these curing accelerators, tertiary amines, imidazoles, and phosphorus compounds are preferably used.

The benzoxazine compound represented by general formula (1) according to the present invention, because of having a lower curing temperature than those of benzoxazine compounds having a hydroxy group known in the art, improves efficiency by time reduction in curing and energy saving and can be used also for a heat-sensitive material (substrate), and thus is very useful. Furthermore, for the cured product thereof, since the compound according to the present invention can melt at a low temperature compared to benzoxazine compounds having a hydroxy group known in the art, the curable resin composition obtained using the compound according to the present invention can be produced and handled at a low temperature, which is very useful.

EXAMPLES

The present invention will now be described more specifically with reference to Examples.

<Analysis Method>

1. Reaction Solution Composition and Purity Analysis (Gel Permeation Chromatography: GPC)

The purity of benzoxazine compounds synthesized was defined as the area percentage of the benzoxazine compounds determined by this analysis.

Apparatus: HLC-8320/manufactured by Tosoh Corporation

Detector: differential refractometer (RI)

[Measurement Conditions]

Flow rate: 1 mL/min

Eluent: tetrahydrofuran

Temperature: 40° C.

Wavelength: 254 nm

Measurement sample: One gram of a benzoxazine compound-containing composition was 200-fold diluted with tetrahydrofuran.

2. Curing Properties Evaluation

The curing properties evaluation of the benzoxazine compounds synthesized was performed by differential scanning calorimetry (DSC) under the following operating conditions. The exothermic peak temperature was used as a curing temperature.

[Measurement Conditions]

Apparatus: DSC7020/manufactured by Hitachi High-Tech Science Corporation

Heating rate: 10° C./min

Measurement temperature range: 30° C. to 400° C.

Measurement atmosphere: nitrogen, 50 mL/min

Measurement sample: benzoxazine compounds synthesized, 3 mg

3. Melt Temperature Evaluation

The measurement of the melt temperature of the benzoxazine compounds synthesized was performed using an aluminum block heater.

Apparatus: HOTB624K hot dry bath with aluminum block/manufactured by AS ONE Corporation Heating rate: 1° C./min Measurement temperature range: 30° C. to 130° C.

For every 10° C. increase, the temperature was held for about 10 minutes to check the melting state of the benzoxazine compound.

Measurement sample: benzoxazine compounds synthesized, 1.0 g

Measuring vessel: glass vial (body diameter x total length: φ15×60 mm)

4. Dynamic Viscoelasticity Measurement (Hereinafter Referred to as DMA) for Heat Resistance Evaluation of Cured Product of Benzoxazine Compound The heat resistance evaluation of cured products of the benzoxazine compounds synthesized was performed by glass transition temperature (Tg) measurement using dynamic viscoelasticity measurement under the following operating conditions.

[Measurement Conditions]

Apparatus: DMA Q800 (manufactured by TA Instruments Japan Inc.)

Jig: dual cantilever

Frequency: 1 Hz

Temperature: 30° C. — 250° C. (2° C./min)

Measurement sample: test pieces obtained by the method described later

Example 1 (Synthesis of Compound According to Present Invention Represented by Chemical Formula Below)

[Chem. 22]

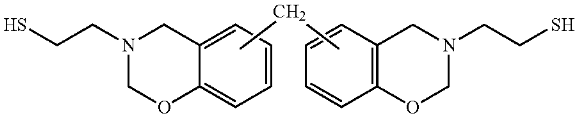

In a 500 mL four-necked flask equipped with a thermometer, a stirrer, a condenser, and a dropping funnel, 31 g (0.15 mol) of bisphenol F (binuclear structure content, 90.1 wt %; isomer ratio thereof: bis(2-hydroxyphenyl)methane, 18.8 wt %; 2-hydroxyphenyl-4-hydroxyphenylmethane, 49.3 wt %; and bis(4-hydroxyphenyl)methane, 31.9 wt %; polynuclear structure content, 9.9 wt %), 20 g of 94% paraformaldehyde, and 57 g of toluene were loaded. After the reaction vessel was purged with nitrogen, the temperature of the mixed solution was adjusted to 60° C. Thereafter, 24 g of 2-aminoethanethiol was added dropwise into the four-necked flask using a dropping funnel over 1 hour while maintaining the temperature at 60° C. After completion of the dropwise addition, stirring was further performed at 60° C. for 2 hours. The composition of the reaction solution was analyzed by GPC according to the above analysis method, revealing that the percentage of the target compound present in the reaction solution was 41 area %.

After completion of the reaction, toluene and water were removed by reduced-pressure distillation at 50° C. The pressure during the distillation was gradually reduced so as to finally reach 2.4 kPa. The composition containing the target compound was taken out to obtain 59 g of the target compound (purity: 41%, compounds with molecular weights higher than that of the target compound: 59 area %).

The results of $^1$H-NMR analysis confirmed that the target compound having the above chemical structure was obtained.

$^1$H-NMR analysis (400 MHz, solvent: $CDCl_3$, reference material: tetramethylsilane)

1.32-1.95 (2H, brm), 2.91-3.05 (4H, m), 3.07-3.22 (4H, m), 3.64-4.13 (10H, m), 6.66-7.12 (6H, m).

Example 2

The reaction was performed in the same manner as in Example 1 with the following changes: bisphenol F, 97 g (0.48 mol); 94% paraformaldehyde, 62 g; toluene, 121 g; the temperature before and after the dropwise addition of amine, 50° C.; 2-aminoethanethiol, 75 g. The composition of the reaction solution was analyzed by GPC according to the above analysis method, revealing that the percentage of the target compound present in the reaction solution was 65 area %.

After completion of the reaction, toluene and water were removed by reduced-pressure distillation at 50° C. The pressure during the distillation was gradually reduced so as to finally reach 1.5 kPa. The composition containing the target compound was taken out, solidified by cooling, then pulverized, and dried at 60° C. and 1.5 kPa to obtain 208 g of the target compound (purity: 56%, compounds with molecular weights higher than that of the target compound: 44 area %).

Example 3

The reaction was performed in the same manner as in Example 1 with the following changes: 94% paraformaldehyde, 74 g; the temperature before and after the dropwise addition of amine, 30° C.; the time of stirring after completion of the dropwise addition of amine, 3 hours. The composition of the reaction solution was analyzed by GPC according to the above analysis method, revealing that the percentage of the target compound present in the reaction solution was 88 area %.

After completion of the reaction, alkali washing was performed using a 3% aqueous sodium hydroxide solution, and water washing was then performed until the pH of the reaction solution became 7 or less. Thereafter, toluene and water were removed by reduced-pressure distillation at 30° C. The pressure during the distillation was gradually reduced so as to finally reach 2.3 kPa. After the solvent was removed to some extent, the remaining solvent was further removed at 90° C. and 2.8 kPa. The composition containing the target compound was taken out, solidified by cooling, and then pulverized to obtain 156 g of the target compound (purity: 75%, compounds with molecular weights higher than that of the target compound: 25 area %).

Example 4 (Synthesis of Compound According to Present Invention Represented by Chemical Formula Below)

[Chem. 23]

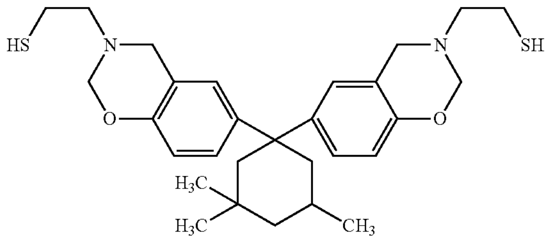

The reaction was performed in the same manner as in Example 1 except that a 1 L four-necked flask equipped with a thermometer, a stirrer, a condenser, and a dropping funnel, 97 g (0.31 mol) of 1,1'-bis(4-hydroxyphenyl)-3,3,5-trimethylcyclohexane, 48 g of 94% paraformaldehyde, 48 g of 2-aminoethanethiol, and 180 g of toluene were used, the temperature before the dropwise addition of amine was adjusted to 30° C., and stirring was further performed at 30° C., 40° C., and 50° C. each for 3 hours after completion of the dropwise addition of amine. The composition of the reaction solution was analyzed by GPC according to the above analysis method, revealing that the percentage of the target compound present in the reaction solution was 73 area %.

After completion of the reaction, alkali washing was performed using a 3% aqueous sodium hydroxide solution, and water washing was then performed until the pH of the reaction solution became 7 or less. Thereafter, toluene and water were removed by reduced-pressure distillation at 30° C. The pressure during the distillation was gradually reduced so as to finally reach 4.2 kPa. After the solvent was removed to some extent, the remaining solvent was further removed at 90° C. and 20 kPa. The composition containing the target compound was taken out, solidified by cooling, and then pulverized to obtain 188 g of the target compound (purity: 71%, compounds with molecular weights higher than that of the target compound: 29 area %).

The results of $^1$H-NMR analysis confirmed that the target compound having the above chemical structure was obtained.

$^1$H-NMR (400 MHz, solvent: $CDCl_3$, reference material: tetramethylsilane)

0.25-0.44 (3H, m), 0.76-1.02 (7H, m), 1.11 (1H, dd), 1.36 (1H, d), 1.75-2.05 (2H, m), 2.33 (1H, brm), 2.59 (1H, brm), 2.77-3.22 (8H, m), 3.54-3.79 (4H, m), 3.86-4.07 (4H, m), 6.51-7.04 (6H, m), 9.07-10.3 (2H, brm).

Comparative Synthesis Example 1 (Synthesis of Comparative Example Compound A Represented by Chemical Formula Below)

[Chem. 24]

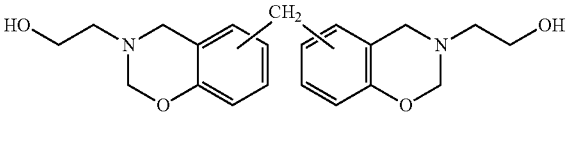

In a 1 L four-necked flask equipped with a thermometer, a stirrer, a condenser, and a dropping funnel, 97 g (0.49 mol) of bisphenol F, 62 g of 94% paraformaldehyde, and 121 g of toluene were loaded. After the reaction vessel was purged with nitrogen, the temperature of the mixed solution was adjusted to 70° C. Thereafter, 60 g of 2-aminoethanol was added dropwise into the four-necked flask using a dropping funnel over 2 hours while maintaining the temperature at 70° C. After completion of the dropwise addition, stirring was further performed at 70° C. for 3 hours. The composition of the reaction solution was analyzed by GPC according to the above analysis method, revealing that the percentage of the target compound present in the reaction solution was 51 area %.

After completion of the reaction, toluene and water were removed by reduced-pressure distillation at 70° C. The pressure during the distillation was gradually reduced so as to finally reach 4.8 kPa. The composition containing Comparative Example Compound A was taken out, solidified by cooling, then pulverized, and dried at 60° C. and 1.5 kPa to obtain 173 g of a Comparative Example Compound A-containing composition (purity: 53%, compounds with molecular weights higher than that of Comparative Example Compound A: 47 area %).

The results of $^{1}$H-NMR analysis confirmed that a benzoxazine compound having the above chemical structure, i.e., Comparative Example Compound A, was obtained.

$^{1}$H-NMR analysis (400 MHz, solvent: $CDCl_3$, reference material: tetramethylsilane)

2.43-2.72 (2H, brm), 2.71-3.16 (4H, m), 3.41-4.09 (12H, m), 4.69-5.01 (4H, m), 6.49-7.07 (6H, m).

Comparative Synthesis Example 2

An Fa-type benzoxazine compound (Comparative Example Compound B) widely used as a benzoxazine compound and represented by the following structure was synthesized as described below.

[Chem. 25]

(B)

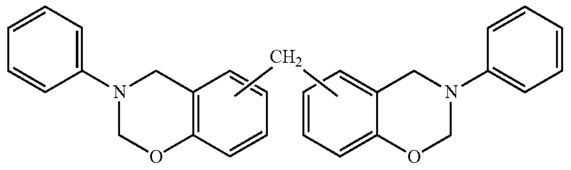

In a 1 L four-necked flask equipped with a thermometer, a stirrer, a condenser, and a dropping funnel, 83 g (0.41 mol) of bisphenol F, 77 g of aniline, 56 g of 94% paraformaldehyde, and 153 g of toluene were loaded. After the reaction vessel was purged with nitrogen, the temperature of the reaction solution was adjusted to 90° C. Thereafter, stirring was performed for 2 hours while maintaining the temperature at 90° C. The composition of the reaction solution was analyzed by GPC according to the above analysis method, revealing that the percentage of the target Comparative Example Compound B present in the reaction solution was 71 area %.

After completion of the reaction, toluene and water were removed by reduced-pressure distillation at 90° C. The pressure during the distillation was gradually reduced so as to finally reach 20 kPa. The composition containing Comparative Example Compound B was taken out to obtain 178 g of a Comparative Example Compound B-containing composition (purity: 69%, compounds with molecular weights higher than that of Comparative Example Compound B: 31 area %).

Comparative Synthesis Example 3 (Synthesis of Comparative Example Compound C Represented by Chemical Formula Below)

[Chem. 26]

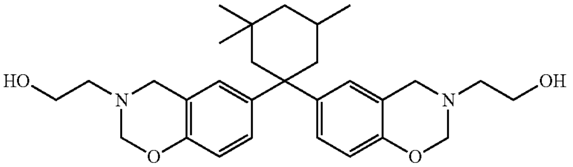

In a 1 L four-necked flask equipped with a thermometer, a stirrer, a condenser, and a dropping funnel, 124 g (0.4 mol) of 1,1-bis(4-hydroxyphenyl)-3,3,5-trimethylcyclohexane, 63 g of 92% paraformaldehyde, and 230 g of toluene were loaded. After the reaction vessel was purged with nitrogen, the temperature of the mixed solution was adjusted to 30° C. While maintaining the temperature, 49 g of 2-aminoethanol was added dropwise into the four-necked flask using a dropping funnel over 2 hours. After completion of the dropwise addition, stirring was further performed at 30° C. for 4 hours. The composition of the reaction solution was analyzed by GPC according to the above analysis method, revealing that the percentage of the target compound present in the reaction solution was 79 area %.

After completion of the reaction, alkali washing was performed using a 3% aqueous sodium hydroxide solution, after which 350 g of toluene was added, and water washing was performed until the pH of the water-washed solution became 7 or less. Thereafter, toluene and water were removed by reduced-pressure distillation at 60° C. The pressure during the distillation was gradually reduced so as to finally reach 4.8 kPa. After the solvent was removed to some extent, the remaining solvent was further removed at 90° C. and 9.8 kPa to obtain 183 g of the target compound (purity: 76%, compounds with molecular weights higher than that of the target compound: 24 area %).

The results of $^{1}$H-NMR analysis confirmed that a benzoxazine compound having the above chemical structure, i.e., Comparative Example Compound C, was obtained.

$^{1}$H-NMR analysis (400 MHz, solvent: $CDC_3$, reference material: tetramethylsilane)

0.30-0.40 (3H, m), 0.84 (1H, m), 0.90-1.00 (6H, m), 1.10 (1H, m), 1.76-2.02 (2H, m), 2.32 (1H, m), 2.58 (1H, m), 2.81-3.07 (4H, m), 3.57-4.05 (8H, m), 4.73-4.90 (4H, m), 6.50-7.12 (6H, m).

<Curing Properties Evaluation and Melt Temperature Evaluation>

For the benzoxazine compounds obtained in Examples 2 and 4 and Comparative Synthesis Examples 1 to 3, curing properties evaluation and melt temperature evaluation were performed according to the above analysis methods. The results are listed in Table 1.

TABLE 1

| Benzoxazine compound | Curing temperature (° C.) | Melt temperature (° C.) |
|---|---|---|
| Example 2 Compound | 187 | 60 |
| Example 4 Compound | 193 | 90 |
| Comparative Example Compound A | 220 | 120 |
| Comparative Example Compound B | 250 | 60 |
| Comparative Example Compound C | 224 | 110 |

As shown in Table 1, it has become clear that Example 2 Compound and Example 4 Compound, which are the inventive compounds, cure at lower temperatures than Comparative Example Compounds A and C and the widely used Fa-type benzoxazine compound (Comparative Example Compound B), which indicates that the use of the novel benzoxazine compound represented by general formula (1) according to the present invention can lower the temperature during the process of molding a thermosetting resin, enabling higher efficiency due to reduced time of heating and cooling and saved energy, and in addition the benzoxazine compound can be used also for a heat-sensitive material (substrate) and thus is very useful.

As shown in Table 1, it has become clear that the compound of Example 2, which is the inventive compound, melts at a lower temperature than Comparative Example Compound A, Comparative Example Compound C, and Comparative Example Compound B. The curable resin composition obtained using the novel benzoxazine compound represented by general formula (1) according to the present invention can be produced and handled at a low temperature, and thus is very useful.

Preparation of Test Piece of Cured Product of Example 2 Compound

Example 2 Compound was melted and degassed for about 2 hours until free of bubbles, and cast into a preheated silicone casting plate for DMA measurement. Thereafter, heating at 175° C. for 2 hours in a dryer (DP32, manufactured by Yamato Scientific Co., Ltd.) followed by cooling was performed. The surface of the resulting plate-like resin cured product was polished with sandpaper to thereby prepare a test piece of the cured product.

Method of Preparing Test Piece of Cured Product of Example 4 Compound

Example 4 Compound was melted and degassed for about 2 hours until free of bubbles, and cast into a preheated silicone casting plate for DMA measurement. Thereafter, heating at 140° C.→150° C.→160° C.→180° C.→200° C./each for 2 hours in a dryer (DP32, manufactured by Yamato Scientific Co., Ltd.) followed by cooling was performed. The surface of the resulting plate-like resin cured product was polished with sandpaper to thereby prepare a test piece of the cured product.

Method of Preparing Test Piece of Cured Product of Comparative Example Compound A A silicone casting plate for DMA measurement was filled with Comparative Example Compound A. Thereafter, heating at 175° C. for 2 hours in a dryer (DP32, manufactured by Yamato Scientific Co., Ltd.) followed by cooling was performed. The surface of the resulting plate-like resin cured product was polished with sandpaper to thereby prepare a test piece of the cured product.

<Heat Resistance Evaluation of Cured Product of Benzoxazine Compound>

Using the benzoxazine compound test pieces prepared by heat curing according to the methods described above, the glass transition temperature (Tg) of the cured products was measured by DMA. The results are listed in Table 2.

The glass transition temperature (Tg) of Comparative Example Compound B is a value given in Journal of the Japan Institute of Electronics Packaging, Vol. 14, No. 3, pp. 204 to 211, 2011.

TABLE 2

| Benzoxazine compound | Glass transition temperature (Tg) |
|---|---|
| Example 2 Compound | 152 |
| Example 4 Compound | 209 |
| Comparative Example Compound A | 188 |
| Comparative Example Compound B | 169 |

As shown in Table 2, it has become clear that the cured products obtained using Example 2 Compound and Example 4 Compound, which are the inventive compounds, not only exhibit an excellent effect of curing at a low temperature as shown in Table 1, but also have a high glass transition temperature (Tg) and have high heat resistance. In particular, it has become clear that the cured product obtained using Example 4 Compound has a higher glass transition temperature (Tg) than Comparative Example Compound A and the widely used Fa-type benzoxazine compound (Comparative Example Compound B) and has even higher heat resistance.

The invention claimed is:

1. A benzoxazine compound represented by general formula (1):

(1)

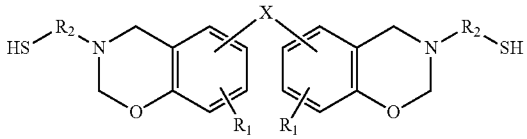

wherein $R_1$ represents a hydrogen atom or an alkyl group having 1 to 6 carbon atoms, $R_2$ represents a divalent group having 1 to 10 carbon atoms, and X represents a single bond, an oxygen atom, a sulfur atom, a sulfonyl group, a carbonyl group, or a divalent group represented by general formula (1a) or general formula (1b), (1a)

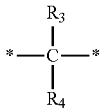

(1b)

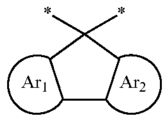

wherein, in general formulae (1a) and (1b), $R_3$ and $R_4$ each independently represent hydrogen, an unsubstituted alkyl group having 1 to 10 carbon atoms, an unsubstituted alkyl halide group having 1 to 10 carbon atoms, or an unsubstituted aryl group having 6 to 12 carbon atoms, $R_3$ and $R_4$ are optionally bonded to each other to together form a cycloalkylidene group having 5 to 20 carbon atoms, $Ar_1$ and $Ar_2$ each independently represent an aryl group having 6 to 12 carbon atoms, and * represents a bonding position directly bonded to the benzoxazine structure.

2. A resin raw material composition comprising the benzoxazine compound according to claim 1.

3. A curable resin composition comprising the benzoxazine compound according to claim 1.

4. The curable resin composition according to claim 3, further comprising at least one selected from the group consisting of epoxy resins, benzoxazine compounds other than the benzoxazine compound represented by general formula (1), phenol resins, and bismaleimide compounds.

5. A cured product obtained by curing the curable resin composition according to claim 3.

6. A curable resin composition comprising the resin raw material composition according to claim 2.

7. The curable resin composition according to claim 6, further comprising at least one selected from the group consisting of epoxy resins, benzoxazine compounds other than the benzoxazine compound represented by general formula (1), phenol resins, and bismaleimide compounds.

8. A cured product obtained by curing the curable resin composition according to claim 4.

9. A cured product obtained by curing the curable resin composition according to claim 6.

10. A cured product obtained by curing the curable resin composition according to claim 7.

11. The benzoxazine compound according to claim 1, wherein X represents the divalent group represented by general formula (1a) wherein $R_3$ and $R_4$ are bonded to each other to together form a cycloalkylidene group having 5 to 20 carbon atoms.

* * * * *